United States Patent [19]
Bao et al.

[11] Patent Number: 5,985,673
[45] Date of Patent: *Nov. 16, 1999

[54] METHOD FOR REGENERATION OF A SENSOR

[75] Inventors: Qingcheng Bao, Tempe; Ian Sorensen, Phoenix; William Glaunsinger, Chandler, all of Ariz.

[73] Assignee: Arizona Baord of Regents, Tempe, Ariz.

[ * ] Notice: This patent issued on a continued prosecution application filed under 37 CFR 1.53(d), and is subject to the twenty year patent term provisions of 35 U.S.C. 154(a)(2).

[21] Appl. No.: 08/632,693

[22] Filed: Apr. 16, 1996

Related U.S. Application Data

[63] Continuation of application No. 08/589,448, Jan. 22, 1996, abandoned, which is a continuation of application No. 08/363,643, Dec. 22, 1994, abandoned.

[51] Int. Cl.⁶ .................................................. G01N 27/04
[52] U.S. Cl. ........................... 436/151; 204/431; 73/23.2; 73/25.03; 73/335.05
[58] Field of Search ...................................... 436/150–157; 422/82.01–82.04; 204/431, 432; 73/23.2, 25.03, 335.02, 335.05

[56] References Cited

U.S. PATENT DOCUMENTS

| | | |
|---|---|---|
| 3,124,771 | 3/1964 | Rohrback . |
| 3,578,409 | 5/1971 | Silverman . |
| 3,714,562 | 1/1973 | McNerney ............... 324/65 R |
| 3,888,110 | 6/1975 | Clark . |
| 3,961,842 | 6/1976 | Jasinski ............... 350/160 R |
| 3,973,192 | 8/1976 | Justi et al. . |
| 4,059,406 | 11/1977 | Fleet ...................... 23/230 R |
| 4,196,427 | 4/1980 | Rudberg . |
| 4,224,280 | 9/1980 | Takahama et al. . |
| 4,313,338 | 2/1982 | Abe ............................. 73/23 |
| 4,338,281 | 7/1982 | Treitinger ................... 422/98 |
| 4,343,768 | 8/1982 | Kimura . |
| 4,358,951 | 11/1982 | Chang ......................... 73/23 |
| 4,362,765 | 12/1982 | Abe .......................... 427/38 |
| 4,387,165 | 6/1983 | Youngblood ............. 436/121 |
| 4,432,224 | 2/1984 | Typpo . |
| 4,453,151 | 6/1984 | Leary et al. . |
| 4,525,266 | 6/1985 | Schmidt et al. .......... 204/412 |
| 4,541,904 | 9/1985 | Lüder ...................... 204/38.3 |
| 4,542,640 | 9/1985 | Clifford . |
| 4,565,786 | 1/1986 | Dunkhase ................. 436/26 |
| 4,580,439 | 4/1986 | Manaka ....................... 73/23 |
| 4,587,104 | 5/1986 | Yannopoulos . |
| 4,592,967 | 6/1986 | Komatsu et al. . |
| 4,706,493 | 11/1987 | Chang ......................... 73/23 |
| 4,724,008 | 2/1988 | Bell ........................... 134/2 |
| 4,830,713 | 5/1989 | Gagescu .................. 204/1 T |
| 4,839,767 | 6/1989 | Yoshioka et al. . |
| 4,911,892 | 3/1990 | Grace ........................ 422/94 |
| 4,928,513 | 5/1990 | Sugihara ................... 73/1 G |
| 4,938,928 | 7/1990 | Koda et al. . |
| 4,953,387 | 9/1990 | Johnson ...................... 73/25 |
| 4,992,244 | 2/1991 | Grate . |
| 5,010,021 | 4/1991 | Bell et al. . |
| 5,042,288 | 8/1991 | Vig ............................. 73/24 |
| 5,087,574 | 2/1992 | Bell et al. . |
| 5,090,232 | 2/1992 | Wakabayashi .............. 73/23 |
| 5,145,645 | 9/1992 | Zakin et al. . |
| 5,201,229 | 4/1993 | Ibe ........................... 73/799 |
| 5,208,162 | 5/1993 | Osborne et al. . |
| 5,238,729 | 8/1993 | Debe ....................... 428/245 |
| 5,243,238 | 9/1993 | Kean . |
| 5,334,351 | 8/1994 | Heinze et al. . |
| 5,356,458 | 10/1994 | Javadi et al. . |
| 5,466,605 | 11/1995 | Glaunsinger et al. . |
| 5,470,756 | 11/1995 | Coles et al. . |
| 5,521,099 | 5/1996 | Glaunsinger et al. . |
| 5,635,136 | 6/1997 | Gluansinger et al. . |

FOREIGN PATENT DOCUMENTS 9015323  12/1990  WIPO .

OTHER PUBLICATIONS

M. A. George et al., "D–Electrical, Spectroscopic, and Morphological Investigation of Chromium Diffusion Through Gold Films," Arizona State University (academic paper), No Date.

George et al., "The Electrical and Structural Properties of Gold Films and Mercury Covered Gold Films." *Thin Sol. Films*, vol. 245, pp. 215–224 (1994).

G. W. Sheets,, "A Multi–Temperature Gas Sensor Fabricated Utilizing Micro–Machining and Integrated Circuit Processing Techniques," Arizona State University (Dissertation 1993).

Cranny et al., "An Investigation into the Viability of Screen Printed Organic Semiconductor Compounds as Gas Sensors," *Inst. Phys. Conf. Ser. No. 111: Int. Conf. on New Materials and Their Applications*, pp. 345–354 (1990).

M. A. George et al., "Electrical, Spectroscopic, and Morphological Investigation of Chromium Diffusion Through Gold Films," *Thin Solid Films*, vol. 189, pp. 59–72 (1990).

(List continued on next page.)

*Primary Examiner*—Lyle A. Alexander
*Attorney, Agent, or Firm*—Baker & Botts LLP

[57] ABSTRACT

A method and apparatus for rapidly and continuously restoring the sensing capacity of thin film sensing elements includes passing a sufficient electrical current through the sensing element to remove from the element selected components from a fluid sample in contact with the sensing element that have an affinity for and are adsorbed and accumulated onto the surface of the sensing element. The passing of current through the sensing element can be accomplished either by applying a constant voltage across the sensing element or by forcing a constant current through the sensing element. The restoration technique removes the components from the sensing element by a combination of resistive heating of the element and electron bombardment of the components on the surface of the element. Moreover, to prevent possible rupture of the sensing element due to electromigration, the current may be alternated in a first direction and then in a second and opposite direction through the sensing element in sequential runs of equal predetermined time intervals.

13 Claims, 21 Drawing Sheets

OTHER PUBLICATIONS

M. A. George et al., "Thermally induced changes in the resistance, microstructure, and adhesion of thin gold films on Si/SiO$_2$ substrates," *J. Vac. Sci. Technol. A.,* vol. 8 No. 3, pp. 1491–1497 (May/Jun., 1990).

J. Janata, *Principles of Chemical Sensors,* Ch. 4, pp. 218–221 (1989).

Kayser et al., "Sensing Devices for Sodium Vapvr Detection, 9 Sensors and Actuators" 323–331 (1986).

J. J. McNerney et al., "Gold Film Technology," *Sensors,* vol. 3 pp. 39, 40, 42 (Feb. 1986).

J. J. McNerney et al., "Mercury Detection by Means of Thin Gold Films," *Science,* vol. 178, pp. 611–612 (Nov., 1972).

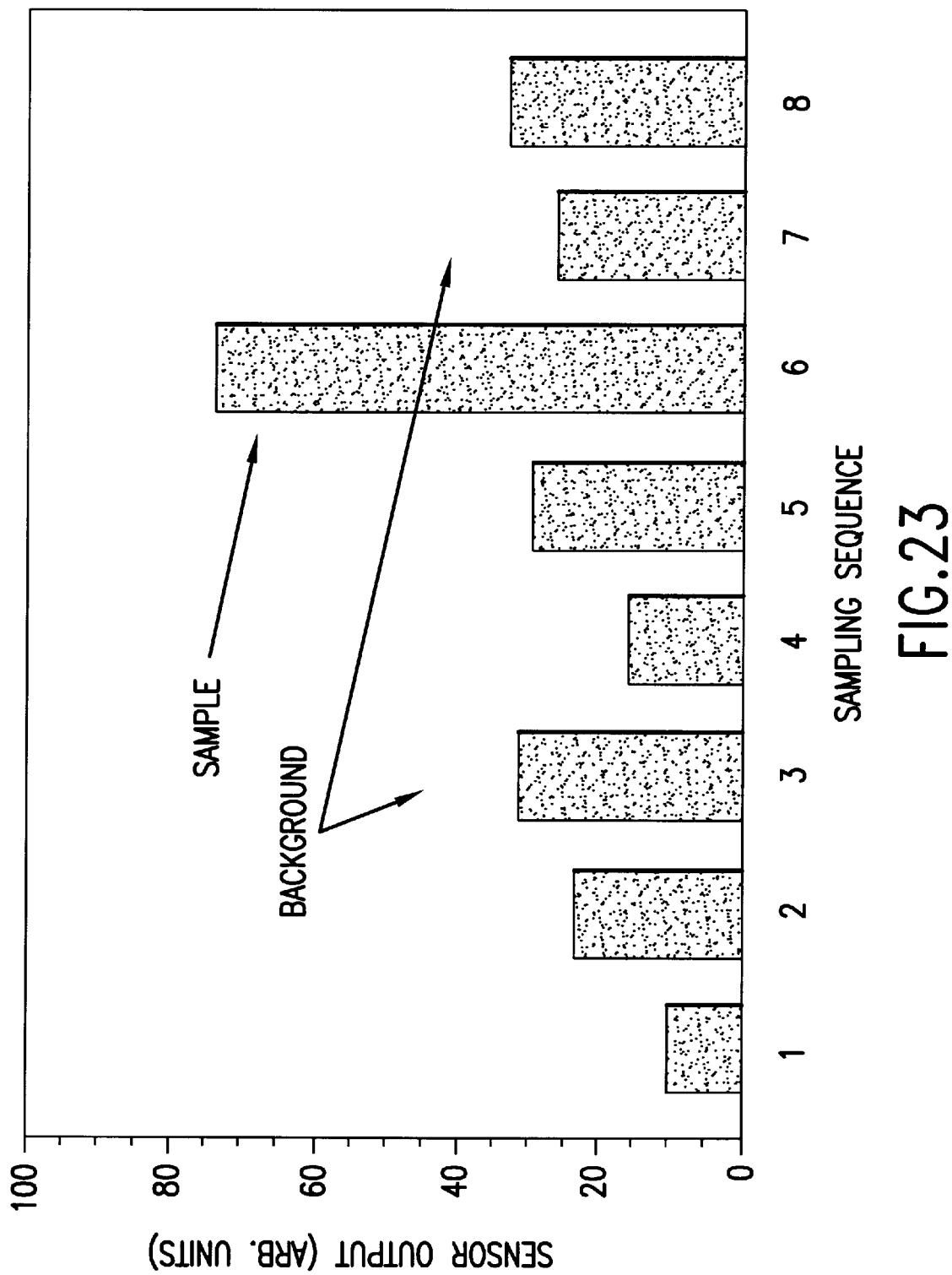

METHOD FOR REGENERATION OF A SENSOR

CROSS REFERENCE TO RELATED APPLICATIONS

This application is a continuation of U.S. patent application Ser. No. 08/589,448, filed Jan. 22, 1996, now abandoned, which is a continuation of U.S. patent application Ser. No. 08/363,643, filed Dec. 22, 1994, now abandoned.

BACKGROUND OF THE INVENTION

The present invention relates generally to sensors for detecting selected chemical components in a fluid mixture and, more particularly, to miniaturized thin metal film sensors for detecting selected components rapidly and continuously and for restoring the sensing capacity of the sensor that decreases with the accumulation of the selected component on the sensor.

Detection of selected components in a fluid mixture, such as toxic or other hazardous materials in air, or other environments, is desirable. For example, during the past decade, there has been an increasing emphasis on prevention, control and minimization of pollution from facilities such as refineries, coal-fired utilities, municipal waste incinerators and wastewater treatment plants. It would be desirable to verify the reduction of such pollution by analyzing, on a more real-time basis, the composition of the off-fluid stream at different locations within the treatment facility. Further, increasingly strict government regulations are leading to requirements that at least end points of such facilities be accurately monitored to ensure that pollutants released into the environment remain below thresholds established by legislative regulations. Additionally, more real-time characterization of process streams, such as those in refinery and petrochemical industries, and in wastewater treatment, is essential for effective feedback control strategies to optimize efficiency and minimize pollution.

These needs call for a chemical sensor meeting at least the following criteria. The sensor should be able to rapidly and repeatedly monitor for the presence of selected components. The sensor should be able to differentiate between the components of interest and to detect a broad dynamic range of concentrations of each selected component. The sensor should have a fast response time with respect to detection of selected components as well as a capability for removal of accumulated components. Additionally, the sensor should be compact, low cost and rugged for operation in extreme environments.

One method for detecting selected components in a fluid mixture is described in U.S. Pat. No. 3,714,562 by McNerney (the "McNerney patent"). The McNerney patent utilizes a thin layer of conductive material having a chemical affinity for the component of interest. When the thin layer is contacted with the fluid, the component, if present, is adsorbed onto the surface of the layer, thereby increasing its electrical resistance. For example, a thin film of gold experiences a measurable rise in resistivity when mercury vapor in a gaseous environment with which the film is in contact is adsorbed onto the film. Thus, the thin film device of the McNerney patent is useful as a sensor of a selected component in the fluid mixture in which the change in resistance of the gold film may be calibrated to detect the percentage of the selected component in the fluid medium by the amount adsorbed on the gold film in a given interval of time.

However, a problem with the above-described sensor is that the selected component, which adsorbs onto the thin film, accumulates on the thin film and eventually saturates all sites available on its surface. This saturation makes the sensor insensitive to future contacts with the selected component and, thus, impairs its sensing capacity. As a result, the sensing capacity of the sensor must be restored by cleansing the thin film to remove the accumulated components from the surface of the thin film.

One method for restoring the sensing capacity of such a sensor is described in U.S. Pat. No. 4,724,008 by Bell et al. (the "Bell Patent"). The Bell Patent describes a method to remove an accumulated reduced sulfur component on the sensing film of an $H_2S$ thin gold film sensor by oxidizing and evolving the sulfur from the sensor and restoring the sensing capacity of the sensor (see col. 1, lines 57–66 of the Bell patent). Such restoration is achieved by a process of either 1) heating the sensor in contact with oxygen to a sufficient temperature (approximately 265° C.) to oxidize and evolve the sulfur from the sensor, or 2) to avoid the need for heating the sensing film to 265° C., reacting ozone with the accumulated sulfur component to oxidize and evolve that component either at room temperature, or, to fully restore the baseline resistance value of the gold film sensor to zero, at approximately 100° C. (see col. 4, lines 3–28 of the Bell patent). The first method, heating the sensor, requires the use of separate heater elements 23, heater switch 26, and rheostat 25, as shown in FIG. 1 of the Bell Patent. However, the use of a separate heater has several disadvantages. First, the heater requires significant electrical power thereby ruling out battery operation for portability. Second, because of the relatively large size and mass of the overall device, an extended period of time is required to heat the sensor and then to wait for the device to return to ambient temperature prior to taking the next measurement. This significantly increases the response time of the device and, thus, does not allow for the rapid and continuous monitoring of selected components. Third, because a chromium adhesive layer is used to attach the gold film to a substrate, the lifetime of the sensor is primarily determined by the interdiffusion between the gold film and the chromium adhesive layer. In particular, after many thermal regenerations, chromium diffuses to the surface of the gold film thereby poisoning the sensor by making its surface insensitive to the selected component.

Moreover, the second method, the use of ozone, requires an ozone generator, as shown in FIG. 1 of the Bell Patent. Also, this method will require the use of heater elements if it is desired to fully restore the baseline resistance value of the gold film sensor to zero.

Additionally, U.S. Pat. No. 4,059,406 by Bernard Fleet (the "Fleet patent") discloses a method for detecting one or more electroactive species in a flow stream by using an electrochemical detector (col. 1, lines 46–48 of the Fleet patent). In particular, the electrochemical detector has an electrochemical thin-layer flow cell adapted to operate on the wall-jet principle and includes a sensor electrode, a solution inlet line, at least one solution exit line and a controller unit for applying a periodically changing voltage to the sensor electrode so that a first part of each cycle of the applied voltage functions as a detecting potential and a second part of each cycle of the applied voltage functions as a cleaning potential (col. 1, lines 32–45 of the Fleet patent). These voltages are required to cause a forward and reverse electrolysis reaction. For example, a detecting potential of 1.2 volts enables a forward reaction to occur, wherein predetermined ions may deposit as an amalgam on the surface of the sensor electrode (col. 4, lines 35–39 of the Fleet patent). Likewise, a cleaning potential of −0.2 volts enables the reverse reaction to occur, wherein the predetermined ions are re-reduced from the surface of the sensor electrode (col. 4, lines 1–5 of the Fleet patent). Thus, the electrochemical detector of the Fleet patent is an electrochemical sensor that utilizes the principles of electrolysis and always requires a voltage to be applied to the sensor electrode to stimulate either a forward or reverse chemical reaction. Moreover, with such a low cleaning potential applied to the sensor electrode (−0.2 volts), cleansing of the sensor electrode is certainly not accomplished by heating the electrode, but rather by electrochemical reactions in which only a negligible amount of current flows through the sensor electrode.

Hence, there exists a need for an improved sensor that better satisfies the aforementioned criteria for rapidly and continuously detecting selected components in a fluid mixture and for restoring the sensing capacity of the sensor due to an accumulation of components being adsorbed onto a surface of a thin film of metal of which the sensor is composed.

SUMMARY OF THE INVENTION

It is an aspect of the present invention to provide an improved method and apparatus for fully restoring the sensing capacity of a sensor.

Another aspect of the present invention is to restore the sensing capacity of a sensor by injecting a current through the sensor itself for a predetermined time interval to cleanse the sensor of accumulated components adsorbed thereon.

Still another aspect of the present invention is to restore the sensing capacity of a sensor by applying a constant voltage across the sensor for a predetermined time interval or until the sensor reaches a predetermined temperature for a predetermined time interval to cleanse the sensor of accumulated components adsorbed thereon.

Yet another aspect of the present invention is to restore the sensing capacity of a sensor by forcing a constant current through the sensor for a predetermined time interval or until the sensor reaches a predetermined temperature for a predetermined time interval to cleanse the sensor of accumulated components adsorbed thereon.

Another aspect of the present invention is to restore the sensing capacity of a sensor by alternately injecting a current in a first direction and then in a second and opposite direction through the sensor for equal predetermined time intervals to inhibit electromigration that could rupture the thin film of which the sensor is composed.

Still another aspect of the present invention is to provide a method for restoring the sensing capacity of a sensor without requiring a separate heating element or the use of ozone as a reactant.

Yet another aspect of the present invention is to provide an apparatus for rapidly and continuously detecting selected components in a fluid mixture.

Another aspect of the present invention is to provide for increased stability of a sensor by creating an identical reference element that can be fabricated by surface passivation.

Still another aspect of the present invention is to provide a sensor for detecting selected components in an oxygenated environment as well as an oxygen-free environment. In this regard, the sensitivity can be enhanced by operation in oxidizing atmospheres to provide a chemical amplification of the sensor response.

In accordance with the above and other aspects, the present invention provides a method and apparatus for restoring a sensing capacity of a sensing element composed of a thin metal film. When the sensing element is exposed to a selected component having a chemical affinity for the former, the selected component adsorbs onto the surface of the sensing element. As more of the component adsorbs onto the sensing element, the sensitivity of the sensing element decreases. The present invention provides a regeneration circuit for passing an electrical current through the sensing element for a predetermined time interval. This passage of current through the sensing element can be accomplished by either applying a constant voltage across the sensing element or by forcing a constant current through the sensing element. This current can remove the components on the sensor by resistive heating of the sensing element as well as by electron bombardment of the components on the surface of the sensing element. Additionally, the current may be alternated in a first direction and then in a second and opposite direction through the sensing element in predetermined, but equal, time intervals to inhibit electromigration that can rupture the thin film of which the sensing element is composed. Passage of the regeneration current through the sensor itself eliminates the need for an additional component (a heater) and electrical connections thereto, while making the most efficient use of the current to heat only the sensor, thereby minimizing heat wasted by dissipation in other components. Moreover, the small sensor size, as well as its effective thermal isolation via a bridge structure, also minimizes the heat dissipated.

The present invention also provides an apparatus for ongoing rapid and repeated detection of a wide range of selected components, for example, selected components occurring in ultra-low levels such as 1 part per billion up to much higher levels such as several hundred parts per million. The apparatus includes a plurality of sensor modules, each including sensing and reference elements such that when selected chemical components in a gas stream have adsorbed to the surface of the sensing element, a change in the ratio of resistances of the sensing element relative to the reference element results. The apparatus also includes electronic circuitry for detecting such change and for converting such change into a measured concentration of the selected component within the gas stream. The electronic circuitry further includes regeneration circuits for providing both constant-voltage and constant-current regeneration. Additionally, the apparatus includes a flow system for controlling the concentration of the selected component in a gas stream, the flow rate of the gas stream, and the time that a gas stream containing the selected component flows to the sensor modules.

The present invention also provides a method for creating a reference element having a substantially identical temperature coefficient to that of a corresponding sensing element. In particular, first and second thin metal films are contacted with a fluid containing reactive components which have an affinity for the metal films. After a sufficient time, the reactive components saturate the surface of the metal films. The first thin metal film is subsequently regenerated whereby the reactive components adsorbed thereon are removed. Thus, the first thin metal film may operate as a sensing element because its surface has available bonding sites for subsequently adsorbing additional reactive components. However, the second thin metal film is not regenerated and its surface remains saturated with the reactive components. Thus, the second thin metal film may operate as a reference element because its surface is inert to further exposure to the reactive components. Such a reference element is dynamic because it can be easily converted back into an active sensing element by regenerating the reference element and desorbing the reactive components from the reference element. The regeneration may be accomplished by, for example, passing a current through the sensing element as described above.

BRIEF DESCRIPTION OF THE DRAWINGS

The above and other aspects, features and advantages of the invention will become clear from the following detailed description of the best mode presently contemplated for practicing the invention, in conjunction with the accompanying drawings in which:

FIGS. 22 and 23 are bar diagrams respectively illustrating sensor module responses to 579 parts per million and 1.15 parts per million by weight of sulfur in iso-octane.

DETAILED DESCRIPTION OF THE PREFERRED EMBODIMENT AND METHOD

Figure 1:
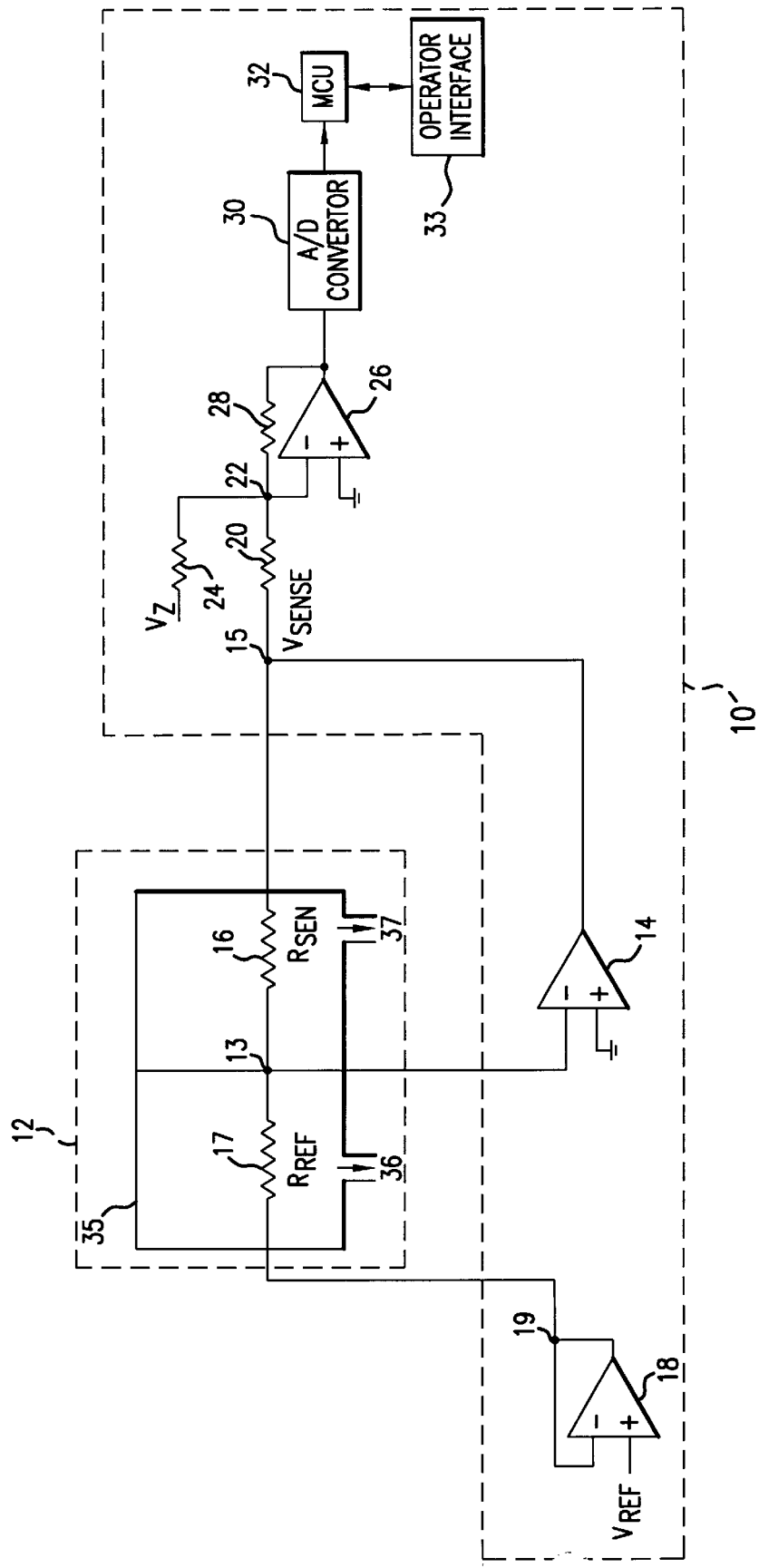
FIG. 1 is a detailed schematic/block diagram of a circuit coupled to a sensor module for sensing and detecting the presence of selected components in a fluid mixture.

Referring to FIG. 1, sensor module 12 and circuit 10 are shown for sensing and detecting the presence of selected components within a fluid sample. Sensor module 12 includes sensing element ($R_{SEN}$) 16 and reference element ($R_{REF}$) 17, respectively. Sensor module 12 further includes housing 35 for encapsulating elements 16 and 17 and for allowing a fluid sample, entering housing 35 at input port 36, to contact resistors 16 and 17. Subsequently, the sample of fluid exits housing 35 via output port 37. The flow system for injecting the sample of fluid into sensor module 12 will be described in detail hereinafter. It is worth noting that housing 35 should be fabricated from materials that are inert to the fluid streams, exhibit no evolution of components that can interfere with the detection of component(s) of interest, and can be manufactured at a reasonable cost. Suitable materials for housing 35 include polymers, metals and ceramics. However, polymeric materials appear to be the best suited for this application due to their ease of fabrication once a suitable mold has been designed.

Sensing element 16 is coupled between circuit nodes 13 and 15, wherein circuit node 15 is coupled to the output of operational amplifier 14. Circuit node 13 is coupled to the inverting input of amplifier 14, while the non-inverting input of amplifier 14 is returned to ground.

Reference element 17 is coupled between circuit node 13 and the output of operational amplifier 18. Amplifier 18 further has a non-inverting terminal coupled to receive reference voltage $V_{REF}$, and an inverting input coupled to the output of amplifier 18.

Circuit node 15 is further coupled through summing resistor 20 to circuit node 22. Additionally, summing resistor 24 has a first terminal coupled for receiving zero point voltage $V_Z$ and a second terminal coupled to circuit node 22.

Circuit node 22 is coupled to the inverting input of operational amplifier 26, while the non-inverting input of amplifier 26 is returned to ground. Resistor 28 is coupled between circuit node 22 and the output of amplifier 26.

The output of amplifier 26 is coupled to an input of analog/digital (A/D) converter 30. The output of A/D converter 30 is coupled to an input of processor/microcontroller unit (MCU) 32.

MCU 32 is coupled to operator interface 33, which may include such components as a keypad and a liquid-crystal display for interfacing MCU 32 with a user.

Briefly, when a fluid sample comes in contact with sensing element 16, selected components having a chemical affinity for the material of which sensing element 16 is composed adsorb to the surface of element 16, thereby increasing the resistance of element 16. This increase in resistance is proportional to the concentration of selected components present in the fluid sample. As a result, this increase in resistance may be sensed and converted into a measured concentration of the selected component in the fluid sample. The increase in electrical resistance is reflected by an increase in a sensing voltage, $V_{SENSE}$, appearing at circuit node 15. Thus, an increase in the sensing voltage can be translated to mean that the sample of fluid contained the selected components. However, it is well known that the electrical resistance of sensing element 16 will also increase as the temperature increases. Thus, it is advantageous to make the change in voltage appearing at circuit node 15 be a function of ratio of resistances having substantially identical temperature coefficients such that varying temperatures will not affect sensing voltage $V_{SENSE}$.

Amplifiers 14 and 18 ensure that sensing voltage $V_{SENSE}$ is a function of the ratio of the resistances of sensing element 16 and reference element 17. In particular, amplifier 18 provides a constant reference voltage at its output that is substantially equal to reference voltage $V_{REF}$. This, in turn, provides a constant current through reference element 17 since circuit node 13 is at virtual ground wherein the sensing current ($I_{SENSE}$) through reference element 17 as well as through sensing element 16 can be expressed as shown in EQN. 1.

$$I_{SENSE} = \frac{V_{REF}}{R_{REF}} \qquad \text{EQN. 1}$$

where $R_{REF}$ is the electrical resistance of reference element 17.

Since circuit node 13 is at virtual ground and the sensing current through sensing element 16 is known, the sensing voltage ($V_{SENSE}$) appearing at circuit node 15 is then the product of the sensing current and the electrical resistance of sensing element 16 as expressed in EQN. 2.

$$V_{SENSE} = V_{REF} \times \frac{R_{SENSE}}{R_{REF}} \qquad \text{EQN. 2}$$

where $R_{SENSE}$ is the electrical resistance of sensing element 16.

From EQN. 2, it can be seen that the sensing voltage is directly proportional to the ratio of the electrical resistances of the sensing element relative to the reference element. Thus, if the sensing and reference elements have the same temperature coefficient of resistance and reference voltage $V_{REF}$ is independent of temperature, temperature changes will not effect the value of the sensing voltage.

Reference element 17 is fabricated to have a temperature coefficient of resistance substantially identical to that of sensing element 16. In particular, reference element 17 is a thin film made substantially identical to that of sensing element 16, with the exception that the surface of element 17 is passivated so that it is not sensitive to and does not adsorb the component to be detected. Thus, element 17, which is to act as the reference element of sensor module 12, is identically matched to sensing element 16, except for the surface passivation layer.

As will be described in greater detail, an exemplary technique for passivating reference resistor 17 with a passivation layer of molecular thickness is to saturate resistor 17 with the component to be detected so that the component accumulates on its exposed thin-film surface until resistor 17 is rendered insensitive to additional exposure of the component. This technique improves detector performance by providing a reference resistor that is both inert to the component to be detected and exhibits a temperature coefficient of resistance that is essentially identical to that of the sensing resistor.

From the foregoing, it should be understood that, during the sensing operation, an increase in the sensing voltage appearing at circuit node 15 is due to selected components being absorbed onto the surface of sensing element 16, thereby increasing the electrical resistance of sensing element 16 relative to the electrical resistance of reference element 17. However, sensing current $I_{SENSE}$ is designed to be small to avoid any resistive heating of sensing element 16 and reference element 17, thereby causing desorption of components adsorbed thereon. Moreover, the increase in resistance of sensing element 16 due to the adsorption of selected components is relatively small, for example, a fraction of a percent of the initial resistance value of sensing element 16. These two factors correspond to a small increase in sensing voltage, for example, on the order if microvolts. Thus, in order to increase accuracy, it would be desirable to amplify the differential increase in sensing voltage before further processing.

Amplifier 26 subtracts a sensor zero-point voltage $V_Z$ from the sensing voltage. Voltage $V_Z$ is the value of the sensing voltage that would appear at circuit node 15 when sensing element 16 is at its initial baseline resistance corresponding to substantially zero selected components being absorbed onto the surface of sensing element 16. As a result, if no selected components are present in the fluid sample, then no selected components absorb onto the surface of sensing element 16 and, thus, the voltage output of sensing amplifier 26 is substantially equal to zero volts. However, if selected components are present in the fluid sample, they are adsorbed onto the surface of sensing element 16, thereby causing its electrical resistance to increase above its initial baseline resistance and the sensing voltage appearing at circuit node 15 to increase above voltage $V_Z$. This difference between the sensing voltage and voltage $V_Z$ is amplified via amplifier 26 and then converted into a digital signal via A/D converter 30.

The digital signal from A/D converter 30 is transferred to MCU 32 for converting the digital signal to a measured concentration of the selected components in the fluid sample by using a three dimensional correction surface with coefficients determined when sensing element 16 is calibrated. In particular, the correction surface is a three-dimensional surface found by using as x, y and z coordinates the sensor output, the degree of saturation, and the correction factor by which the sensor output is multiplied to obtain the actual concentration. The correction surface is determined by a least-squares fit of the above coordinates to a parametric equation containing four coefficients whose values are determined by the fit. Thus, for any given values of x, y and z, the sensor output can be accurately converted into the actual concentration of the reactive component.

In constructing sensor module 12, sensing element 16 and reference element 17 are each composed of thin films of metal, preferably a pure noble metal such as gold or a mixture of noble metals such as gold and palladium, having a thickness in the range of 50 to 10,000 angstroms (Å). The thin film is attached to an insulating substrate, such as alumina, silicon dioxide, silicon nitride, or a polymer, for example, a film of polyimide, by means of a thin layer of metallic adhesive material. This polymer can be acid provided the heat dissipated into the polymer is sufficiently low to prevent deformation or decomposition. Generally, the metallic adhesive will be chosen from a group of metals having affinity for the substrate and having solid solubility in the metal film to be attached. For example, the metallic adhesive may be chromium, titanium, nickel or aluminum.

An exemplary method of attaching thin metal films to a substrate is fully disclosed in co-pending U.S. patent application Ser. No. 08/353,448, entitled "Selected Area Adhesion and Surface Passivation of Metal Films", and assigned to the assignee of the instant invention. The subject matter of such co-pending U.S. patent application is incorporated by reference herein.

Briefly, the co-pending patent application describes a method of attachment that provides adequate adhesion of the metal film to the substrate for structural integrity, and yet eliminates the adverse surface passivation effects of the metallic adhesives.

Figure 2:
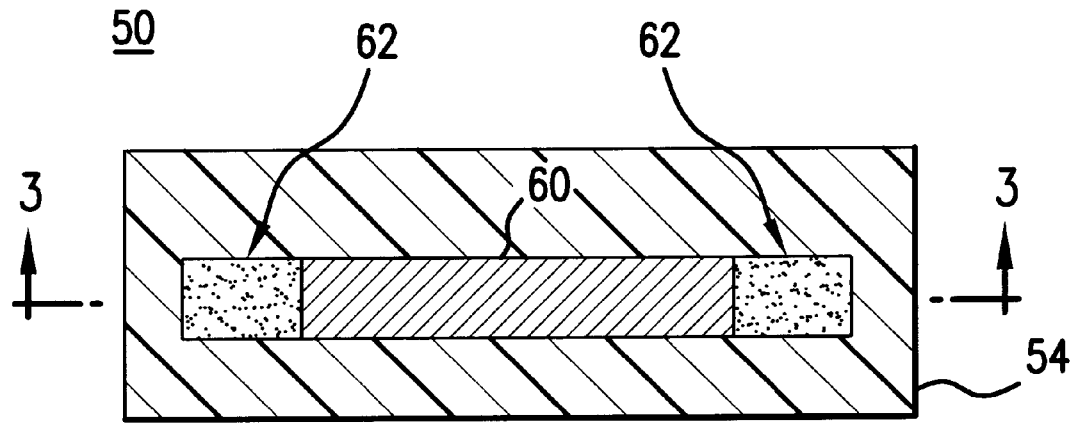
FIGS. 2 and 3 are top and cross sectional views of a sensor device comprising a thin metal film affixed on a substrate with a metallic adhesive selectively placed therebetween.
Figure 3:
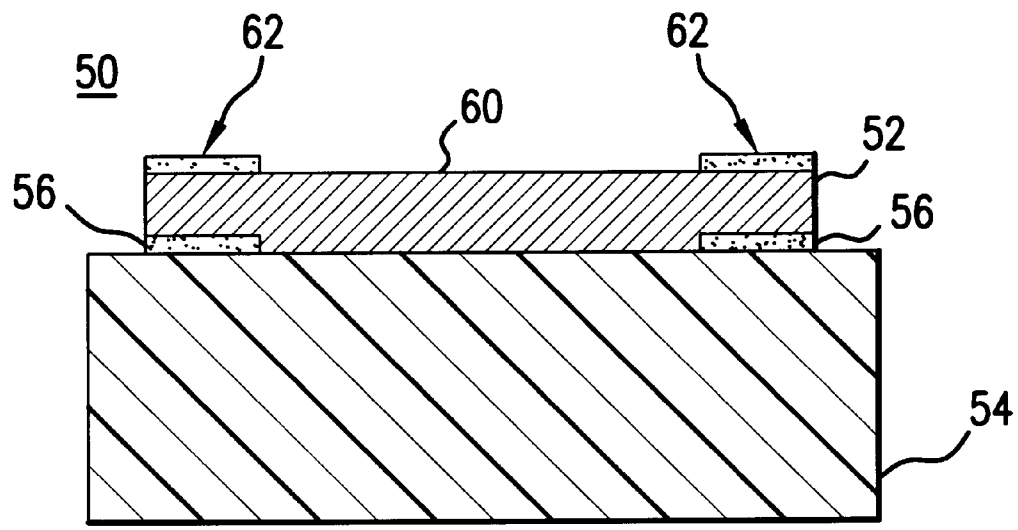

In particular, referring to FIGS. 2 and 3, top and cross sectional views of sensor device 50 are shown. The cross sectional view of FIG. 3 is taken along line 3—3 of FIG. 2. It is understood that device 50 may correspond to sensing element 16 of FIG. 1. Device 50 includes thin metal film 52 on substrate 54, with metallic adhesive 56 selectively placed therebetween.

In a preferred embodiment, thin metal film 52 comprises a gold, or other noble metal-based, film having a thickness in the range of about 5 Å to about 2000 Å, but preferably about 750 Å. Metallic adhesive 56 comprises a layer of chromium having a thickness of about 20 Å to about 1000 Å, but preferably about 200 Å. Substrate 54 is a polyimide thick film having a thickness in the range of 5 microns to 500 microns, but preferably about 75 microns. As shown in FIG. 2, adhesive material 56 is deposited atop substrate 52 in only selected regions to control the passivation occurring atop film 52. For example, adhesive material 56 may be deposited only in selected regions of thin metal film 52 when the latter is deposited to obtain a desired degree of adhesion, or only underneath regions of film 52 where electrical contact pads are to be made.

Device 50 may be fabricated by directing the deposition of metallic adhesive 56 onto only selected areas of substrate 54, as mentioned above, by using masks for relatively large-area deposits (greater than 10 microns) and using standard lithographic methods for smaller-area deposits (less than 0.2 microns). This deposition is then followed by deposition of thin-metal film 52 over adhesive 56 and directly onto substrate 54 such that a portion of film 52 contacts adhesive 56 while another portion contacts substrate 54. Metallic adhesive 56 and thin film 52 can be deposited subsequently in an evaporation system operating at a pressure less then $10^{-6}$ torr to minimize any oxidation of the metallic adhesive prior to application of the thin film. It is worth noting that the deposition of film 52 would include, on its top surface, a dip located between the area where adhesive 56 was not applied to substrate 54 to account for surface contour differences on which film 52 is deposited due to the presence of underlying adhesive layers 56. However, because such dip is quite small, it is not shown for simplicity.

Accordingly, some atoms of metallic adhesive 56 will form bonds with substrate 54 and some with thin film 52. The remainder of atoms of metallic adhesive 56 will remain bonded only to one another. Further, film 52 inherently includes numerous grain boundaries that are capable of providing a path for the unbonded atoms of metallic adhesive 56 to migrate to the top surface of film 52. As a result, if device 50 is exposed to an atmosphere containing oxygen, strong thermodynamic forces cause the unbonded atoms of metallic adhesive 56 to migrate through the grain boundaries of film 52 to form stable surface compounds atop film 52, thereby forming passivation layers 62 atop film 52. It is worth noting that device 50 may be heated to substantially advance ion migration and the passivation process.

For a thin film whose thickness is much less than its planar dimensions, such grain boundary diffusion causes the migrating ions of metallic adhesive 56 to move in a direction substantially normal to the surface of the substrate. As a result, the pattern of the passivation layers occurring atop film 52 will be substantially identical to the pattern of the underlying metallic adhesive. Thus, any passivation forming atop thin film 52 is substantially confined to an area defined by the underlying interfacial metallic adhesive. This phenomenon can be used to achieve a desired degree of adhesive enhancement while controlling thin-film surface passivation by placing the metallic adhesive in only selected areas, such as where adhesion is to be enhanced or where passivation occurring atop film 52 is desired, such as where electrical contact pads will later exist.

In summary, by placing adhesive layers 56 only in areas that will be adjacent to the ends of film 52 when the latter is deposited, passivation layers 62 forming atop film 52 will exist only in areas defined by the underlying interfacial metallic adhesive. As a result, device 50 includes thin film 52 that is securely attached to substrate 54. However, a portion of the surface of film 52 is not passivated, and there remains an exposed, unpassivated, sensor region 60 for use in detecting selected components.

In a preferred embodiment of the present invention, sensor module 12 includes sensing element 16 and reference element 17 positioned on the same side of a substrate. This is not possible in the prior art represented by the Bell patent because of the need for a heater element interleaved between the sensing and reference elements. As will be explained hereinafter, the present invention does not require a heater element.

Figure 4:
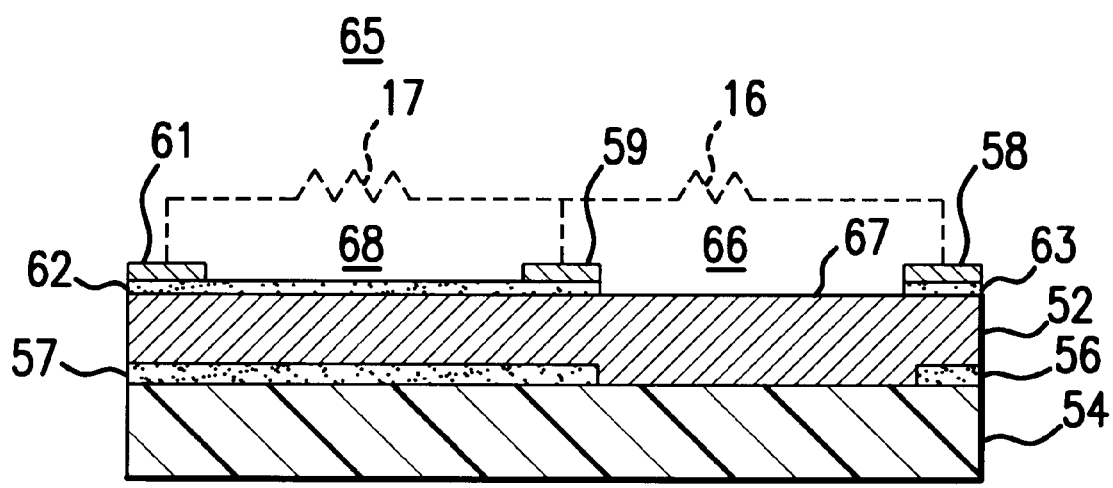
FIG. 4 is a cross sectional view of a sensing element and a reference element being integrated on a same side of a substrate.

In particular, referring to FIG. 4, a cross sectional view of integrated sensing/reference device 65 is shown. It is understood that components shown in FIG. 4 that are identical to components shown in FIGS. 1–3 are identified by like reference numbers. Generally, FIG. 4 illustrates how the concept of selected area adhesion and passivation as described for FIG. 2 and 3 can be used to form a device having sensing and reference elements integrated together on the same side of a substrate. Device 65 comprises active sensing element 66 and inert reference element 68. It is understood that sensing element 66 and reference element 68 may respectively correspond to sensing element 16 and reference element 17 of FIG. 1.

Sensing element 66 has an active surface, as represented by reference number 67, whose purpose is to selectively react with selected chemical components. On the other hand, reference element 68, having the same electrical resistance value as sensing element 66, is provided with a surface that is completely passivated so that reference element 68 cannot respond to chemical components of the types sought to be detected. Electrical connection to sensing element 66 can be made via electrical contact pads 58 and 59, while electrical connection to reference element 68 can be made via electrical contact pads 59 and 61.

Sensing element 66 is fabricated in a similar manner as described for device 50. In particular, the metallic adhesive material is applied atop substrate 54 at only the regions where electrical contact pads 58 and 59 will later reside, but not atop substrate 54 in the region between where electrical pads 58 and 59 will reside, as shown by adhesive layer 56 and the right-most portion of adhesive material layer 57. This creates passivation layer 63 as well as the right-most portion of passivation layer 62. However, as can be seen from FIG. 4, sensing element 66 has a substantial portion of the exposed surface of its film unpassivated for adsorbing selected components.

However, reference element 68 is fabricated so that the top surface between electrical contact pads 59 and 61 is fully passivated. In particular, a metallic adhesive material is applied atop substrate 54 in both the regions where electrical contact pads 59 and 61 will later reside and the region between where electrical pads 59 and 61 will reside, as shown by adhesive layer 57. Due to the migration of the metallic adhesive as described above, passivation layer 62 is formed atop film 52 that essentially passivates reference element 68, thereby precluding adsorption of the components to be detected. It is understood that the passivation of reference element 68 may change its electrical resistance value so that it is no longer exactly equal to that of unpassivated sensing element 66. However, this slight change in resistance can be easily accounted for by determining the ratio of resistances of elements 66 and 68 and then compensating for any measured differences by using a precise, variable resistor. Moreover, this compensation may be performed automatically by electronic circuitry as is understood by one of ordinary skill in the art.

By placing both the reference and sensing elements adjacent to each other and on the same side of a substrate as shown in FIG. 4, many advantages are achieved. First, the fabrication of both the sensing and reference elements is facilitated. Second, the electrical contact pads of the sensing and reference elements may be wire bonded by conventional techniques. Third, the location of the sensing and reference elements is not constrained when compared to the restrictions of the prior art sensors, as represented by the Bell patent.

Figure 5:
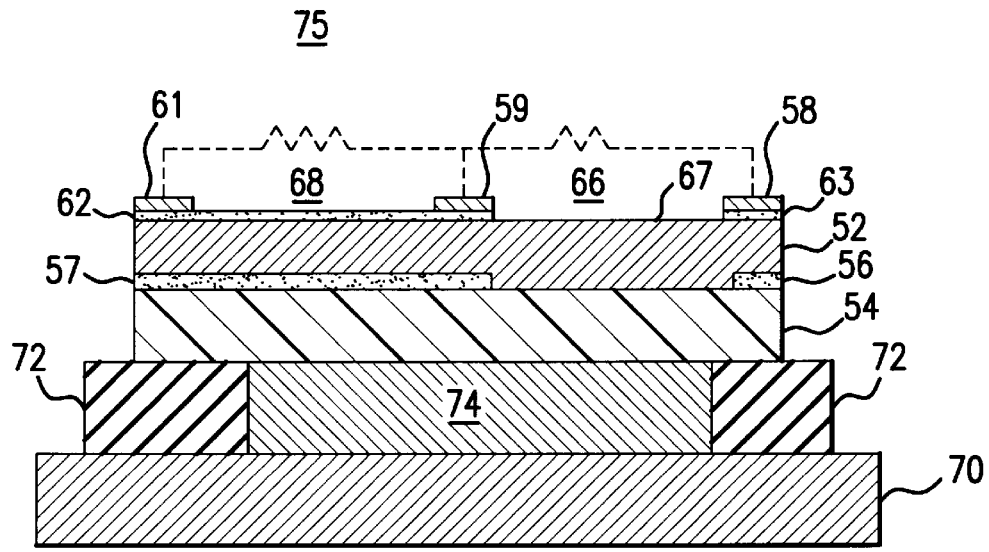
FIGS. 5 and 6 are cross sectional and top views of an assembly device including the integrated sensing and reference elements of FIG. 4.
Figure 6:
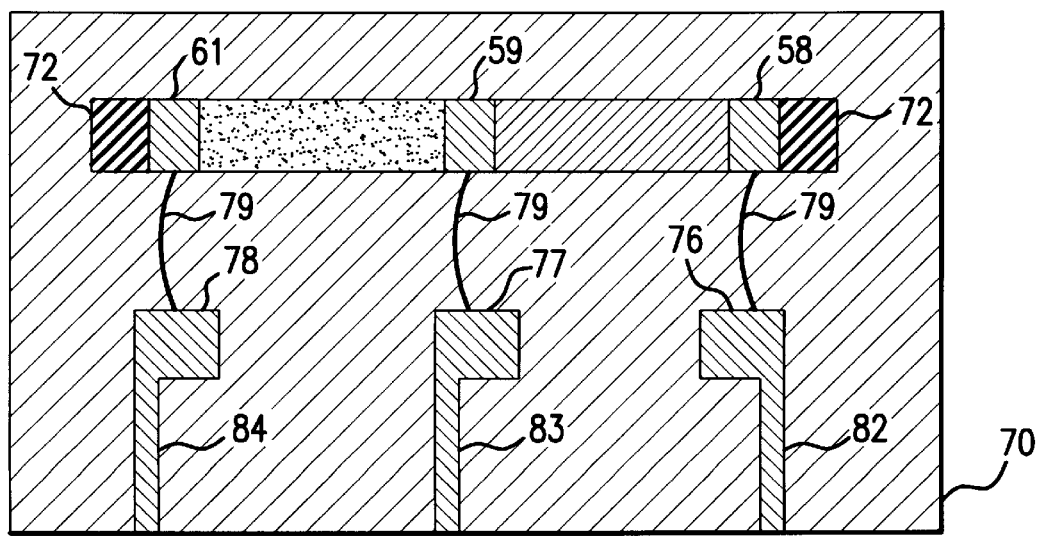

Referring to FIGS. 5 and 6, there is illustrated cross sectional and top views of assembly device 75 that includes sensing/reference device 65 of FIG. 4 being mounted on assembly board 70. Components shown in FIGS. 5 and 6 that are similar to components shown in FIG. 4 are identified by like reference numbers. Assembly device 75 further includes pillars 72 positioned between substrate 54 and assembly board 70 for providing good thermal insulation between substrate 54 and board 70 via insulating barrier 74, such as air. Electrical contact pads 58, 59 and 61 may be respectively wire bonded to electrical contact pads 76–78 on assembly board 70 via wire bonds 79. In this fashion, electrical connection to sensing element 66 is made via contact pads 76 and 77, while electrical connection to reference element 68 is made via contact pads 77 and 78. Additionally, assembly board 70 includes electrical leads 82–84 for connection to contact pads 76–78, respectively. It is understood that electrical leads 82–84 may be respectively coupled to circuit nodes 15, 13 and 19 of FIG. 1.

Figure 7:
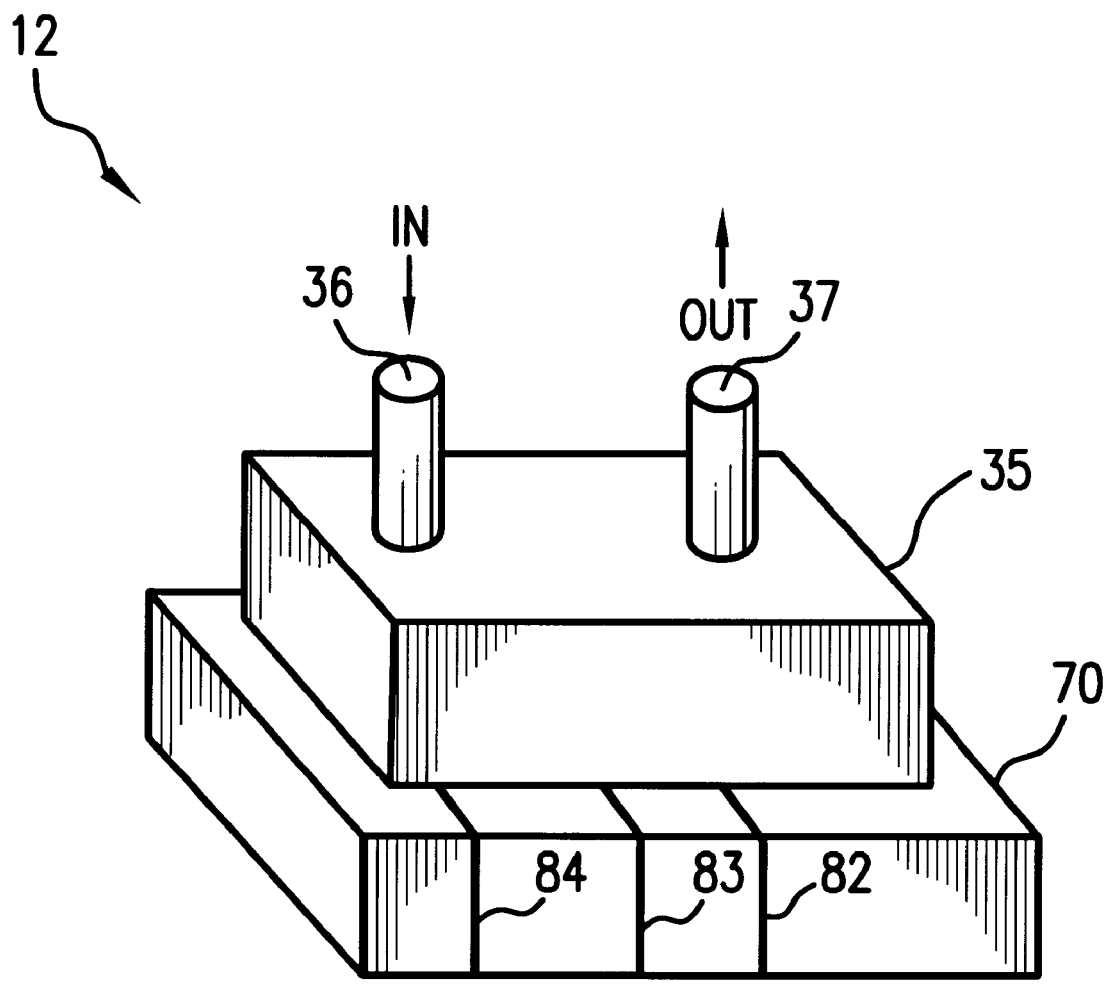
FIG. 7 is a pictorial diagram of the sensor module of FIG. 1.

Referring to FIG. 7, a pictorial diagram of sensor module 12 is shown, including housing 35 for encapsulating assembly device 75. As discussed above, a sample of fluid, which may or may not include the component to be detected, is injected into housing 35 via input port 36 to expose integrated sensing/reference device 65 to the sample of fluid. The sample of fluid is subsequently pumped out of housing 35 through output port 37 via a pump (not shown). Any change in resistance of sensing element 66 relative to reference element 68 is detected by circuit 10, as described above, wherein elements 66 and 68 may respectively correspond to elements 16 and 17 of FIG. 1.

After sufficient exposure to the selected components, the available sites on the exposed surface of sensing element 16 that allow for adsorption of the selected components become depleted. When this happens, the adsorbed selected components saturate the surface of sensing element 16 and it becomes less sensitive to additional exposure to the selected component. This substantially decreases the efficiency of the device as a sensor such that the resistance of sensing element 16 will not change much, if at all, when contacted with a fluid sample including the selected component. Thus, in order to maintain an effective sensor, the sensing capacity of sensing element 16 must be restored by removing the accumulated component from element 16.

Sensing element 16 can be regenerated by simply thermally desorbing the adsorbed components by heating sensing element 16 to a sufficiently high temperature to thermally activate the desorption process. Prior art methods, such as one disclosed in the Bell patent, include an underlying heater that is activated to heat up the sensing resistor. However, as previously discussed, the use of a heater requires significant power and time to regenerate the sensing device, disfavors the sensing and reference devices from being on the same side of a substrate and increases the overall size of the integrated device.

Current-Driven Sensor Regeneration

The present invention provides a method and circuits for restoring the sensing capacity of sensing element 16. In particular, when the surface of sensing element 16 becomes saturated with the selected component, it is desired to regenerate the sensing capacity of sensing element 16 by cleansing the accumulated adsorbed components from sensing element 16. Regeneration may be desired, for example, when the sensing voltage $V_{SENSE}$ reaches a predetermined threshold indicative of sensing element 16 being saturated by a predetermined percentage. During regeneration, the present invention causes a sufficiently high electrical current to pass through sensing element 16 for a predetermined time interval, for example, five seconds, to sufficiently cleanse the components adsorbed to the surface of sensing element 16. This regeneration current ($I_{REGEN}$) is substantially larger than sensing current $I_{SENSE}$, for example, current $I_{REGEN}$ may be approximately 10 times the value of current $I_{SENSE}$. This regeneration current causes the temperature of sensing element 16 to increase, thereby activating the thermal desorption process. Additionally, this regeneration current may also induce desorption by electron bombardment of the adsorbed components on the surface of sensing element 16 due to the high flux of electrons passing through the sensing element. This method of regeneration can be faster and more efficient than conventional heating methods because components can be desorbed not only by resistive heating, but also by electron bombardment.

The passage of current through sensing element 16 can be accomplished by either applying a constant voltage across sensing element 16, or by forcing a constant current through sensing element 16.

Figure 8:
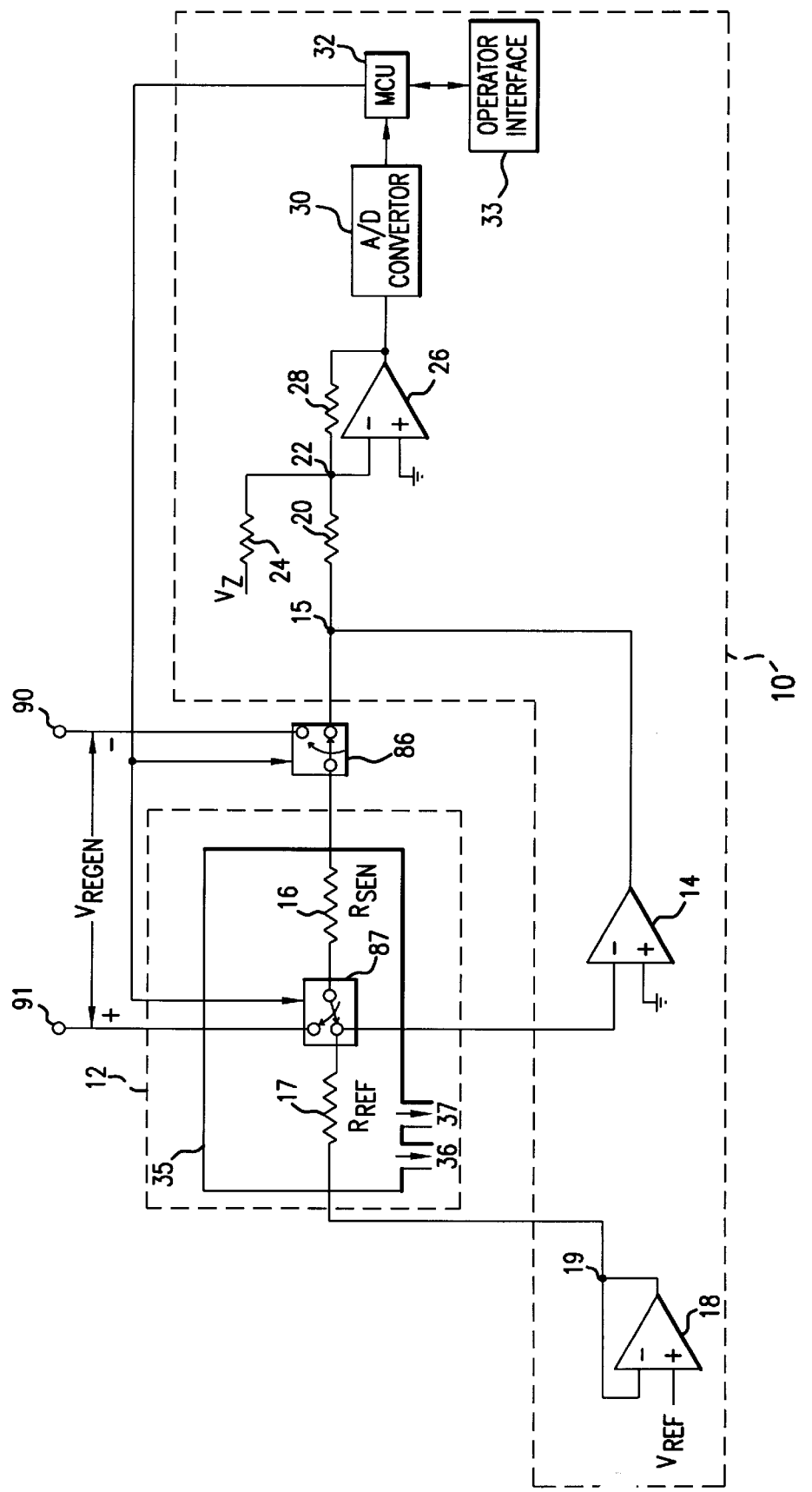
FIG. 8 is a detailed schematic/block diagram of the circuit of FIG. 1 including a regeneration circuit for applying a constant voltage across a sensing element.

Referring to FIG. 8, circuit 10 is shown including a regeneration circuit for applying a constant voltage across sensing element 16. The regeneration circuit comprises switches 86 and 87 for de-coupling sensing element 16 from sensor module 12 and circuit 10 and for applying a constant voltage across sensing element 16 to force current therethrough to cleanse sensing element 16 of accumulated adsorbed components. In particular, switches 86 and 87 respectively include first terminals coupled across power supply terminals 90 and 91, across which a regeneration voltage, $V_{REGEN}$, is applied.

A second terminal of switch 86 is coupled to a first terminal of sensing element 16 while a second terminal of switch 87 is coupled to a second terminal of sensing element 16.

A third terminal of switch 86 is coupled to a first terminal of resistor 20, while a third terminal of switch 87 is coupled to a first terminal of reference element 17.

In operation, when it is desired to regenerate sensing element 16, switches 86 and 87, in response to a control signal from MCU 32, switch the first and second terminals of sensing element 16 from being respectively coupled to resistors 20 and reference element 17 to being respectively coupled to power supply terminals 90 and 91. In this manner, sensing element 16 is switched out of sensor module 12 and circuit 10 and a constant regeneration voltage $V_{REGEN}$ is applied across sensing element 16.

Figure 9:
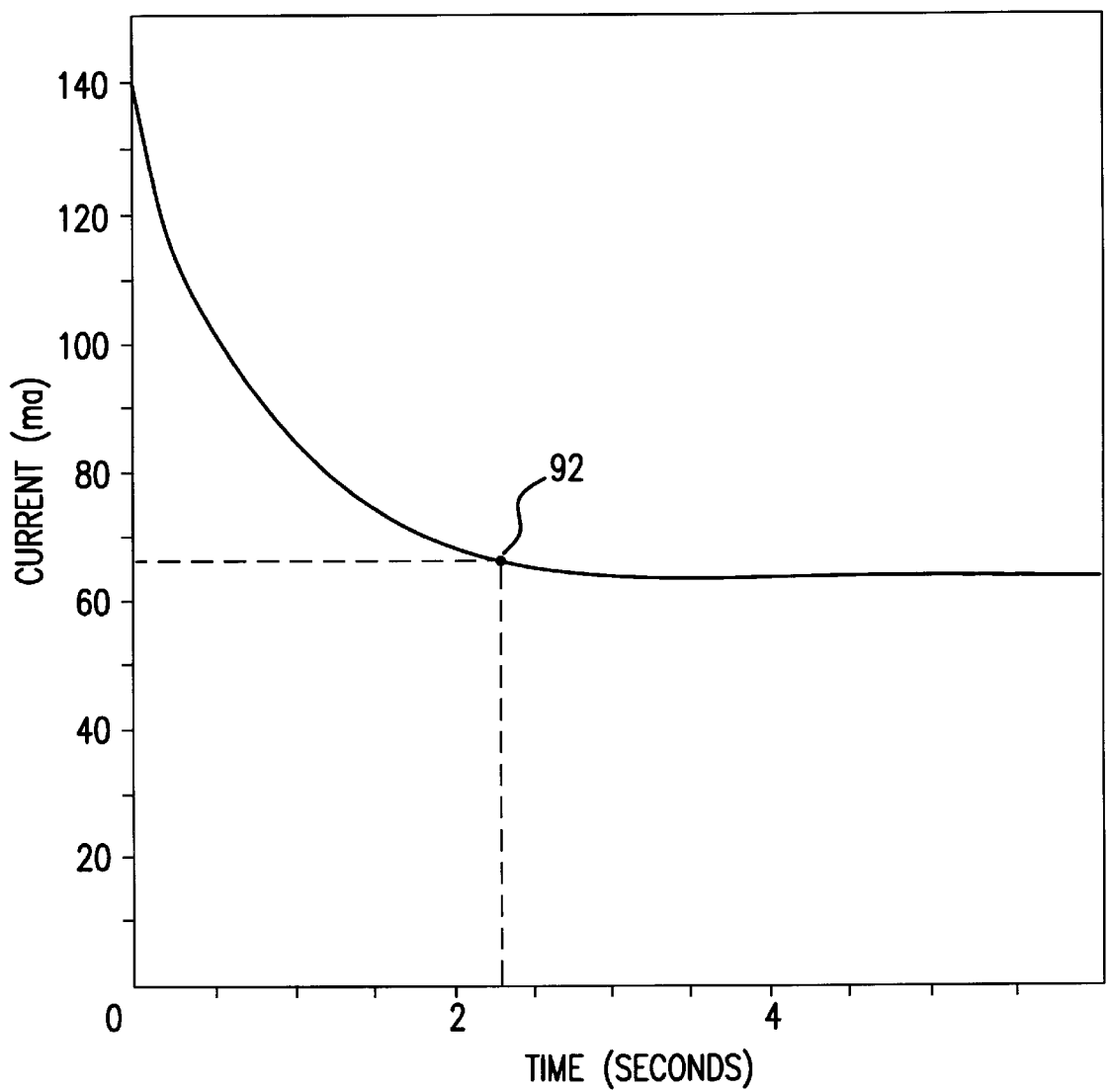
FIG. 9 is graphical diagram illustrating the temporal variation of a typical current passing through the sensing element during constant-voltage regeneration.

Referring to FIG. 9, a graphical diagram is shown illustrating the temporal variation of a typical current passing through sensing element 16 for constant-voltage regeneration. The abscissa axis represents time in seconds, while the ordinate axis represents current in milliamps. The constant voltage applied across sensing element 16 was 11 volts. As shown in FIG. 9, a current surge of about 150 milliamps occurs when the 11 volts is initially applied across sensing element 16. However, after about 2 seconds, a steady state current of about 65 milliamps is established as illustrated by reference number 92. Moreover, this steady state current resulted in a steady state operating temperature of about 350° C. A constant voltage of 11 volts was chosen since it was determined that higher voltages above 11 volts produced a negligible change of sensing element 16 in both initial baseline resistance and sensitivity to hydrogen sulfide. But, it is understood that voltages greater than 11 volts could be used albeit more power consumption.

Figure 10:
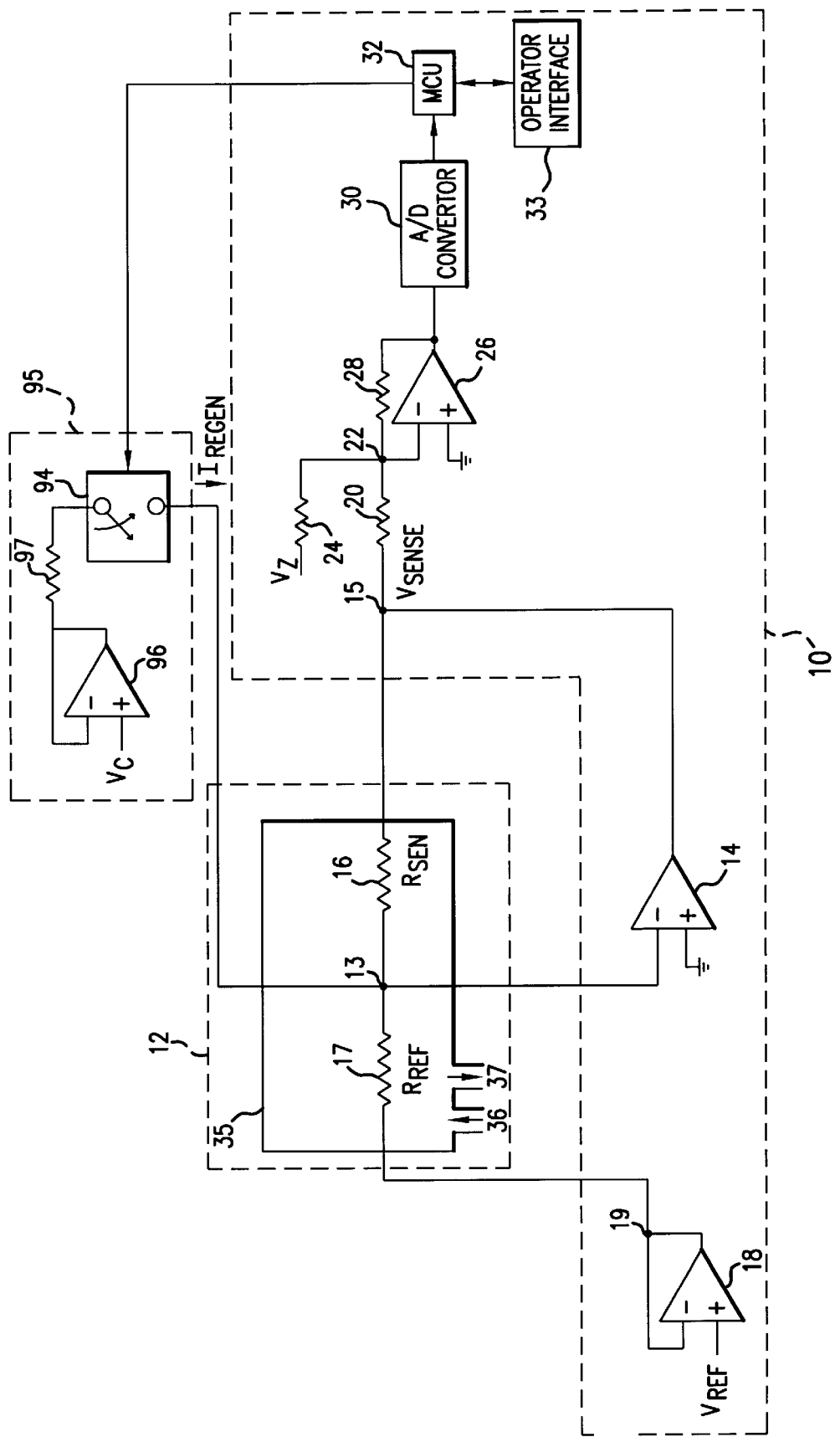
FIG. 10 is a detailed schematic/block diagram of the circuit of FIG. 1 including a regeneration circuit for forcing a constant current through a sensing element.

Referring to FIG. 10, circuit 10 is shown including regeneration circuit 95 for providing constant-current regeneration. It is understood that components shown in FIG. 210 that are identical to components shown in FIG. 1 are identified by the same reference numbers. Regeneration circuit 95 includes switch 94 having a first terminal coupled to circuit node 13 and a second terminal coupled for receiving a constant current.

The constant current is generated by operational amplifier 96 and resistor 97. In particular, amplifier 96 has a non-inverting input coupled to receive a control voltage ($V_C$) and an inverting input coupled to its output as well as through resistor 97 to the second terminal of switch 94.

In operation, amplifier 96 maintains a constant voltage of $V_C$ at its output, such that when the first terminal of switch 94 is coupled to circuit node 13, via a control signal from MCU 32, a constant regeneration current, $I_{REGEN}$, is established. This regeneration current is forced through sensing element 16 and can be expressed as shown in EQN. 3.

$$I_{REGEN} = \frac{V_C}{R_{97}} \quad \text{EQN. 3}$$

where $R_{97}$ is the electrical resistance of resistor 97.

Figure 11:
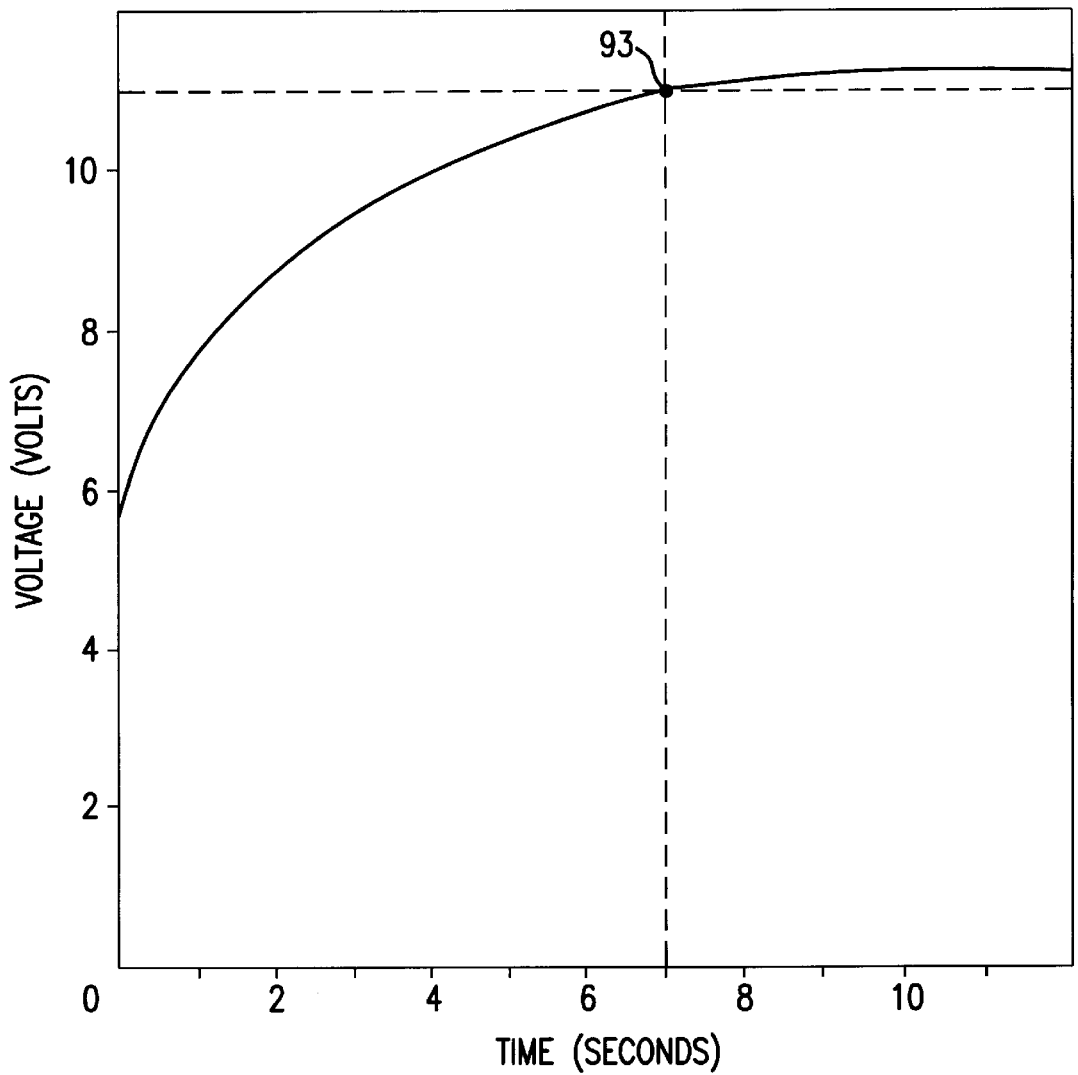
FIG. 11 is graphical diagram illustrating the temporal variation of a typical voltage appearing across the sensing element during constant-current regeneration.

Referring to FIG. 11, a graphical diagram is shown illustrating the temporal variation of a typical voltage drop appearing across sensing element 16 during constant current regeneration. The abscissa axis represents time in seconds while the ordinate axis represents voltage in volts. The constant current forced through sensing element 16 was chosen to be 65 milliamps, so that the voltage across sensing element 16 eventually reached approximately 11 volts, as indicated by reference number 93. This voltage of at least 11 volts was maintained for at least five seconds.

In both constant-voltage and constant-current regeneration, the temperature of sensing element 16 can be determined by measuring the current passing through the element. This provides immediate feedback for temperature control as well as avoids the need for additional temperature-sensing elements, as required by the prior art. In particular, by measuring the current passing through sensing element 16 immediately after the start of the voltage regeneration, and then periodically during the heating of sensing element 16, MCU 32 can monitor the percentage increase in the resistance of sensing element 16. This increase in resistance can then be converted into an increase in temperature using the thermal coefficient of resistance of sensing element 16. In this manner, regeneration may be terminated either after a predetermined time interval, or after the resistance of sensing element 16 has increased to a predetermined value, indicating that a predetermined temperature has been reached, for a predetermined time interval. For the latter temperature control mode, adjustments can be made to the regeneration voltage/current to maintain a constant power dissipation by the sensing element, and thus, a constant temperature for the sensing element.

The method of current-driven regeneration has been demonstrated wherein a device similar to assembly device 75 provided a suitable test device that was utilized to obtain test data relating to the present invention, the results of which are discussed in detail below. In particular, the test device included a sensor module having separate sensing and reference elements, each fabricated in a similar manner as device 50 of FIGS. 2–3, wherein the reference element used had its surface passivated so as to be inert to reactive components. Moreover, the sensing and reference elements were constructed in a serpentine configuration, as opposed to a linear configuration. A serpentine configuration is advantageous because it creates a sensing element having a greater exposed surface area for making contact with a fluid sample. However, such a serpentine configuration inherently consumes more area. In particular, the construction and specifications for the test device were as follows. Film 52 was a thin gold film with a serpentine configuration having a thickness of 750 Å. The dimensions of the serpentine configuration was 22,500 microns in total length, with a sensor width of 120 microns. Substrate 54 was composed of polyimide material having a thickness of 75 microns. Pillars 72 were 1-millimeter thick polyimide materials, with air serving as insulating barrier 74. Board 70 was 1-millimeter thick alumina ceramic. Adhesive material 56 and 57 is chromium having a thickness of 200 Å. The areal dimensions of the contact pads were about 750 microns by 500 microns.

The test device was subjected to a series of hydrogen sulfide loadings and regenerations using both constant-voltage and constant-current modes, with a 5-minute waiting period between regenerations wherein sensing element 16 was exposed to air in the absence of hydrogen sulfide to insure that the temperature of element 16 returned to ambient prior to the next cycle of operation. Under the conditions used in this test, the performance of the constant-current mode was identical to that of the constant-voltage mode.

The current-driven regeneration method using either constant-voltage and constant-current modes has many advantages. First, the current-driven regeneration does not require an external heating element, since heating is accomplished by the passage of current directly through the sensing element. Second, regeneration is highly localized in that it is confined to the sensing element only, so that the sensing element is quickly regenerated and rapidly returns to ambient temperature. Third, current-driven regeneration can be more efficient than conventional thermal desorption because desorption can occur not only by heating, but may also be assisted by electron bombardment originating from the high flux of electrons passing through the sensing element.

Furthermore, constant-voltage regeneration is very fast and, thus, can be advantageous for applications requiring rapid and continuous monitoring. However, the slower constant-current regeneration also has some advantages. First, the initial surge in current, as was exhibited in the constant-voltage mode, is avoided. This slower initial heating may increase the lifetime of the sensing element. Second, as the sensing element ages, there may be an increase in baseline resistance leading to a progressively lower final temperature reached during constant-voltage regeneration. This could eventually lead to incomplete regeneration. However, for constant-current regeneration, the increase in resistance will be offset by a corresponding increase in voltage, so that a higher, rather than a lower, final temperature will result to ensure regeneration of the sensing element. However, controlling the regeneration temperature via the sensing element resistance, as discussed previously, can effectively avoid any excursions in regeneration temperature resulting from operating the sensing element in a pure constant-voltage or constant-current mode.

Additionally, the sensor can be regenerated by passing sufficient current through it for a predetermined time interval to the point where the resistance of the sensor no longer displays a substantial change upon continued loading (exposure) of reactive components. The preferred regeneration point is at the end of the linear response region of the sensor, which corresponds to approximately 50% saturation of components on the surface of the sensor, since the sensitivity of the sensor is constant throughout this region. However, the time that the sensor can be exposed to reactive components without regeneration can be maximized by operating the sensor well into the nonlinear response region, a region which immediately precedes the saturation region. While in the nonlinear region, however, the sensitivity of the sensor decreases. But this loss in sensor sensitivity can be compensated for by multiplying the sensor response by a correction factor determined from the sensor calibration curve. For example, for a stream containing 200 ppb of hydrogen sulfide using a gold-film sensor, the maximum sampling frequency is every 5 seconds for the apparatus 140, as determined by the flow system and data processing parameters. With this setup, up to 100 samples can be taken using the linear region of the sensor before the sensor needs to be regenerated. However, while operating in the nonlinear region, up to 200 samples can be taken before the sensor needs to be regenerated. Thus, by operating the sensor in its nonlinear region, more samples can be taken before regeneration is needed and regeneration is inherently performed less frequently. This results in the favorable effect of substantially increasing the lifetime of the sensor. Note that the regeneration time depends on the gas flow rate, since the gas helps cool the sensor. In the above example, 200 seconds were required at a gas flow rate of 36 cm$^3$/min, whereas only 150 seconds were necessary at a flow rate of 72 cm$^3$/min.

For both constant-voltage and constant-current regeneration, it would be advantageous to avoid the undesirable effects of the electromigration, which can result from mass transport of a material (such as gold) under the influence of an impressed direct current (DC) electrical field. Thus, to prevent possible rupture of the thin film of which the sensing element is composed as a result of electromigration, an alternating current (AC), as opposed to a DC current, may be passed through the sensing element. In particular, the alternating current causes current to flow through the sensing element 16 in a first direction and then in a second and opposite direction through the sensing element in equal predetermined intervals, for example, ranging from cycle times in the millisecond range typical of conventional AC power sources to cycle times of several minutes characteristic of a regeneration cycle.

From previous studies of electromigration-induced failures in gold films (See J. C. Blair, et al., J.Appl. Phys., Vol. 43, No. 2, P. 307, 1972), it can be estimated that the mean regeneration time before failure of a gold film of which sensing element 16 is composed should lie in the range of 0.5 to 500 hours of operating time at a regeneration temperature of 350° C. Since the sensing element 16 can be regenerated in less than 3 seconds at 350° C. in the constant-voltage regeneration mode as was shown in FIG. 9, the number of regenerations before electromigration-induced failure can be predicted to be in the range of 600 to 600,000. Moreover, in all tests performed, a DC current has been passed through the sensors, and an average number of regenerations before device failure has ranged from 500 to 5000. These actual results are consistent with the estimated electromigration-induced failure. In view of this, it is preferable to regenerate sensing element 16 by passing current through the element in alternate directions.

Dynamic Reference

As previously discussed, a reference element is usually integrated alongside a sensing element, as shown in FIG. 4. Further, in order to measure the concentration of selected chemical component with a high degree of precision, the reference element should be both inert to the chemical component to be detected and should have the same temperature coefficient of resistance as the sensing element in order to eliminate thermal drift problems.

Reference elements are preferably fabricated by passivating the surface of the reference element, either by depositing a passivating material on the reference surface, or by inducing the migration of a passivating material to the surface of the reference element, as earlier discussed. As an example, a thin film of gold can be rendered inert to chemical components, such as hydrogen sulfide, by depositing a layer of chromium on the surface of the film. The chromium oxidizes on the surface of the film and forms chromia ($Cr_2O_3$). In general, the film is inert to hydrogen sulfide if the chromium coating is thicker than about 10 Å which corresponds to a chromia thickness of about 30 Å. However, the temperature coefficient of resistance of the film is very sensitive to the thickness of the chromium. In particular, for a thin film of gold having a thickness of 750 Å, the temperature coefficient is reduced by about 10% for a 5 Å chromium coating and by about 20% for a 10 Å chromium coating. Further, such thin chromium layers can be difficult to fabricate with uniform thickness and good reproducability. As a result, if both the reference and sensing elements are fabricated by using thin films of gold, the reference element will have a different resistance value than that of the sensing element with respect to varying temperatures. But, in order to provide a sensing device that is capable of measuring selected chemical components with a high degree of precision, it is imperative that both the sensing element and the reference element have substantially the same temperature coefficient, so that the change in resistance of the reference and sensing elements are substantially the same with respect to temperature.

Figure 12A:
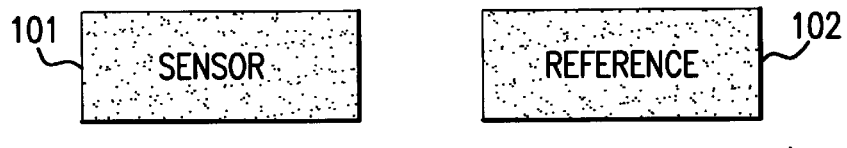
FIGS. 12 (a)–(e) illustrate a method for creating a dynamic reference element having a substantially identical temperature coefficient to that of a corresponding sensing element.
Figure 12B:
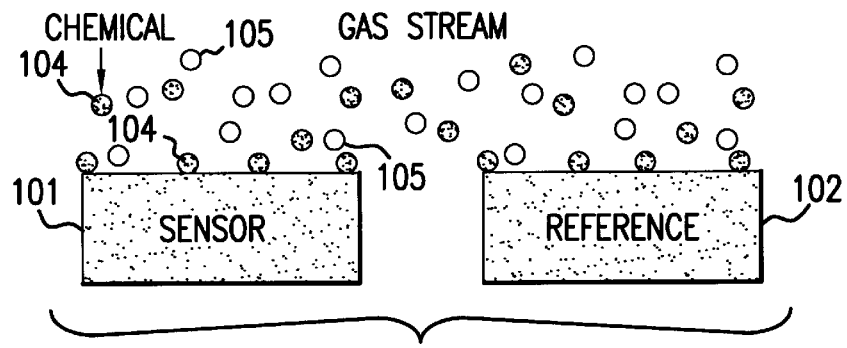
Figure 12C:
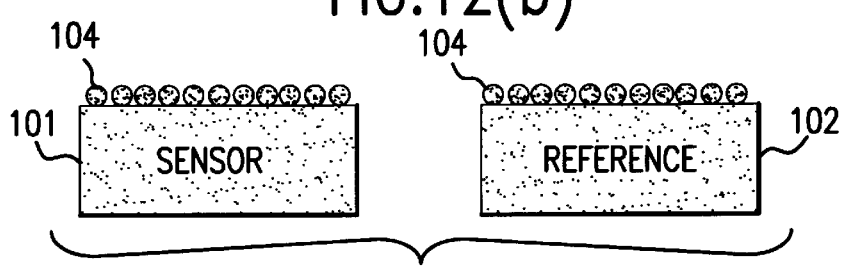
Figure 12D:
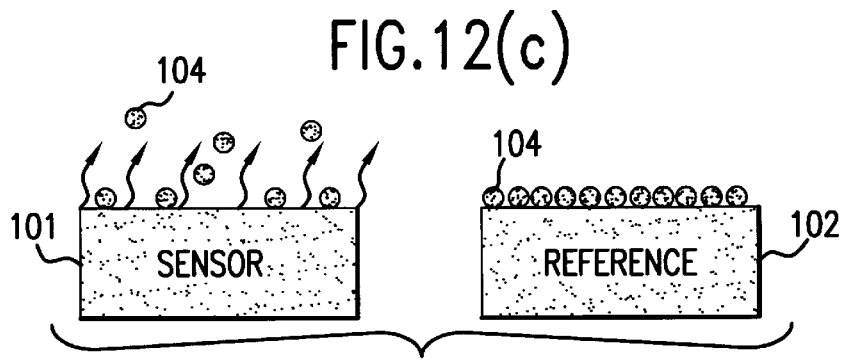
Figure 12E:
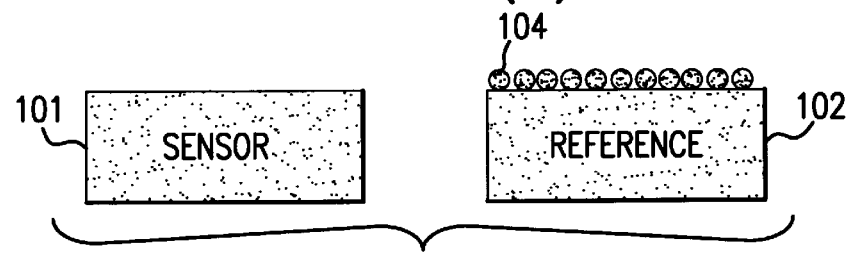

Referring to FIGS. 12(a)–12(e), there is illustrated a method for fabricating a dynamic reference element having a substantially identical temperature coefficient to that of a corresponding sensing element. In FIG. 12(a), identical thin-metal-film elements 101 and 102 are shown. These elements can be fabricated simultaneously, for example, in a manner as previously described, and are then exposed to a gas stream including both reactive components 104 and unreactive components 105, as shown FIG. 12(*b*). It is understood that reactive components 104 have a chemical affinity for the material of which elements 101 and 102 are composed and, thus, reactive components 104 will adsorb onto the surface of elements 101 and 102.

After sufficient exposure to the gas stream, reactive components 104 adsorb to all available bonding sites on the surfaces of elements 101 and 102 and saturate the surfaces of elements 101 and 102, as shown in FIG. 12(*c*).

Element 101 is partially regenerated, as shown in FIG. 12(*d*), and finally fully regenerated, as shown in FIG. 12(*e*) by, for example, the current-driven regeneration method, as discussed in detail above. However, element 102 is not regenerated and its surface remains passivated, as shown in FIGS. 12(*d*) and 12(*e*). In this manner, element 101 remains an active sensing element, while element 102 becomes a reference element. In particular, by passivating the surface of element 102 with reactive components 104, element 102 is rendered inert to subsequent exposure to reactive components 104 because its surface has no available sites for adsorbing additional reactive components. Moreover, since the thickness of the adsorbed reactive component layer is of molecular thickness, the temperature coefficient of element 102 is substantially identical to that of element 101. For example, hydrogen sulfide absorbed on a thin-metal-film sensor forms a molecular layer of only approximately 2 Å thickness. Furthermore, unlike chromium, there is no diffusion of the passivating agent into the sensor element, so that not only is there a negligible increase in the sensor element film thickness, but the composition of the sensor element is unchanged. Thus, the above-described method creates a reference element that is identical to the sensing element, including a substantially identical temperature coefficient, with the exception that the reference element is inert to reactive components.

A reference element created by the above described process is dynamic because it is reversible. For example, a reference element may be created by saturating its surface with adsorbed reactive components, as described above. Subsequently, however, the reference element may be converted back into an active sensing element by cleansing/regenerating its surface of the adsorbed reactive components. This, of course, can be adequately and efficiently accomplished by using the constant-voltage or constant-current regeneration methods, as discussed above.

The reactive components may be included either within the fluid (e.g., gas) stream being monitored, where the reactive components are either present intrinsically in the stream or deliberately added to the stream, or within an external gas stream. If included in the gas stream to be monitored, the creation of the reference element, or the reversal of a reference element back to an active sensing element, can be performed as an integral part of the measurement process of the reactive component within the gas stream, with the understanding that the particular sensor module containing the reference element will provide an inaccurate measurement while undergoing such a reversal process and, thus, its measurement would be discarded.

If, however, the reactive components are not included in the gas stream being monitored, then the passivation process cannot be performed as an integral part of the measurement process of selected components. It is also possible to have reactive components of the gas stream that can from passivation layers of molecular thickness, yet where the passivation process is not reversible. As an example of an irreversible gold-film-sensor deactivation process that can be accomplished via exposure to an external gas stream (ex-situ) is the reaction of the gold film with chlorine gas to form stable surface gold chloride compounds, such as $AuCl$ and $AuCl_3$. This process is described in co-pending U.S. patent application Ser. No. 08/031,610, entitled "Chemical Switch And Method For Detection of Chemical Components". The subject matter of such co-pending U.S. patent application is incorporated by reference herein.

The stability of a dynamic reference element created by the process illustrated in FIG. 12 has been demonstrated using the test device as described above. In particular, hydrogen sulfide was selected as the reactive chemical component because it exhibits the strongest bonding energy to the gold-film surface of any gas currently tested, but yet can be completely removed from the surface of a gold film at temperatures exceeding 300° C. Hydrogen sulfide deactivates the surface of a gold film at a rate that depends upon its concentration and the flow rate of the gas stream. For example, for a hydrogen sulfide concentration of 218 parts per billion flowing at a gas flow rate of 36 $cm^3$/minute, a gold film becomes saturated with hydrogen sulfide in less than 15 seconds.

Figure 13:
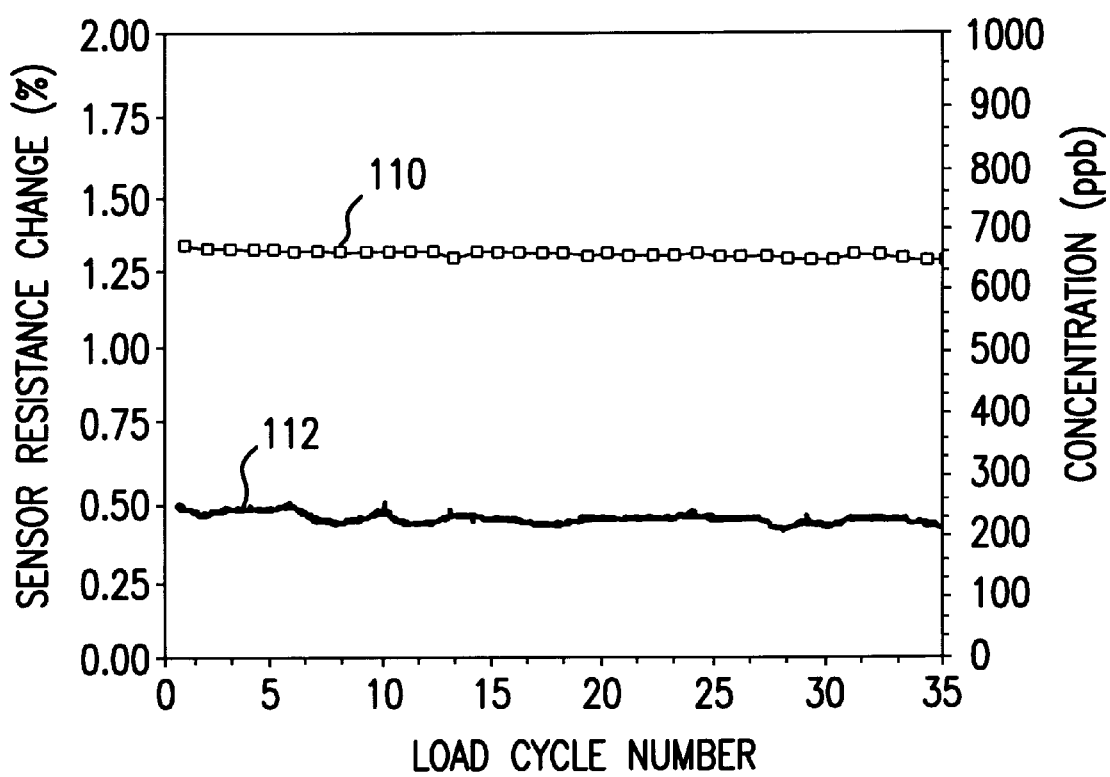
FIG. 13 is a graphical diagram illustrating test results for using the dynamic reference element created by the method illustrated in FIGS. 13 (a)–(e)

Referring to FIG. 13, a graph is shown illustrating typical results of a test using a hydrogen sulfide-passivated element as the reference element in conjunction with an active sensing element in a gas stream consisting of 218 ppb of hydrogen sulfide in air. The horizontal scale represents the load cycle number, wherein, after each loading cycle the sensor was regenerated. The left vertical scale represents the overall percentage resistance change of the sensing element relative to the reference element after each loading cycle prior to regeneration, after which the sensor element is approximately 50% saturated with hydrogen sulfide, and the right vertical scale represents the measured concentration of hydrogen sulfide in ppb.

There were 50 samples taken during each regeneration cycle and for each sample the sensing/reference element pair was exposed to the gas stream for 0.15 seconds, with a 10-second interval between each sample. Regeneration was accomplished by applying 12 volts across the sensing element for 5 seconds. At the end of the regeneration period, the temperature of the sensing element was approximately 380° C., after which a 200-second interval was required to allow the sensing element to return to ambient temperature for another cycle of operation.

Curve 110 represents the overall percentage resistance change of the sensor element relative to the reference element after a complete loading cycle, while curve 112 represents the calculated hydrogen sulfide concentration based on the resistance change of the sensing element relative to the reference element due to adsorption of hydrogen sulfide. If the hydrogen sulfide-passivated reference element changed at all in resistance value during testing, then the percent change of the sensing element relative to the reference element would correspondingly change. This, of course, would result in a changing concentration reading for hydrogen sulfide. However, as can be seen from FIG. 13, the constant response of curves 110 and 112, after a large number of regenerations, demonstrates that a stable reference element has indeed been created by deactivating the surface of the reference element with hydrogen sulfide. Moreover, this dynamic reference element has been calibrated and found to yield results identical to that of a standard chromium-passivated reference element. However, the dynamic reference element of the present invention has a temperature coefficient of resistance that is essentially identical to the sensing element, which substantially eliminates the thermal drift of the sensing element.

From the foregoing, it should be apparent that the dynamic reference resistor created by the process illustrated in FIG. 12 has several advantages. First, it is completely inert to the gas stream, including hydrogen sulfide. Second, the reference element has a substantially identical temperature coefficient as the sensing element because the reference element has been passivated by adsorption of selected components to form a passivation layer of molecular thickness, and not, for example, by forming a relatively thick layer of chromium atop the element. Third, the passivation process is easily reversible in that the reference element can easily be converted back to a sensing element by regeneration. Fourth, the fabrication of both sensing and reference elements is easier and more cost effective because all elements are initially fabricated in the same manner, wherein those that are designated to be reference elements are created by the process illustrated in FIG. 12.

Chemical Amplification

The previous regeneration process test results described above were performed in an oxygen-containing environment such as air. However, other gaseous environments, such as nitrogen, may also be employed. Moreover, the sensitivity of the sensing/reference device can strongly depend upon the chemical composition of components of the gas stream other than those to be selectively measured and can be enhanced/amplified in the presence of certain components. This phenomenon has been demonstrated by comparing the response of the test device described above to hydrogen sulfide in both oxygen-free and oxygen-containing environments.

Tests in an oxygen-free environment were performed using high purity nitrogen gas for the regeneration cycles and a custom-blended fuel gas for the detection cycles. The nitrogen gas contained less than 100 parts per billion of oxygen, while the custom-blended fuel gas contained 75% hydrogen, 10% methane, 10% ethane, 3% propane, 2% isobutane and 16 parts per million of hydrogen sulfide. The use of the fuel gas (a reducing mixture) helps insure that no oxygen is present in the gas stream, since hydrogen is expected to react with any oxygen on the gold film surface of sensing element 16 to form water, which should be desorbed during a regeneration cycle. The fuel gas was diluted with nitrogen at a ratio of 16 to 1 (16:1), so that the hydrogen sulfide concentration in the mixed gas stream was 1 ppm.

In a typical test, the sensor module was thoroughly flushed with nitrogen to remove all oxygen inside the system. The gas flow rate was set at 36 $cm^3$/minute. Since the sensing element can be completely regenerated at voltages exceeding 11 volts in less than 5 seconds, as discussed above, the regeneration voltage and regeneration time were respectively set at 12 volts and 5 seconds to insure complete sensor regeneration.

For oxygen-free testing, each load cycle consisted of a hydrogen sulfide detection cycle followed by a regeneration cycle and a subsequent cool-down period of 200 seconds. There were 15 samples in each loading cycle, and for each sample the sensing element was exposed to the 1 ppm hydrogen sulfide stream for 0.15 seconds, which corresponds to about 0.15 nanograms of hydrogen sulfide absorbed on the surface of the sensing element per sample assuming a hydrogen sulfide sticking probability of 100% to the gold-film surface. There was a 10-second interval between successive samples, during which the hydrogen sulfide was filtered out of the stream. The timing of the test sequences was controlled by a computer. The exposure times and intervals were accurately controlled using a personal computer (PC) with basic software and a Data Translation DT2801 A/D I/O Interface that permitted the PC to turn solenoids on and off as well as to collect and store the resulting data.

The same procedure was used for tests in an oxygen-containing environment except that pure, dry air (21% oxygen) was used instead of pure nitrogen.

Figure 14:
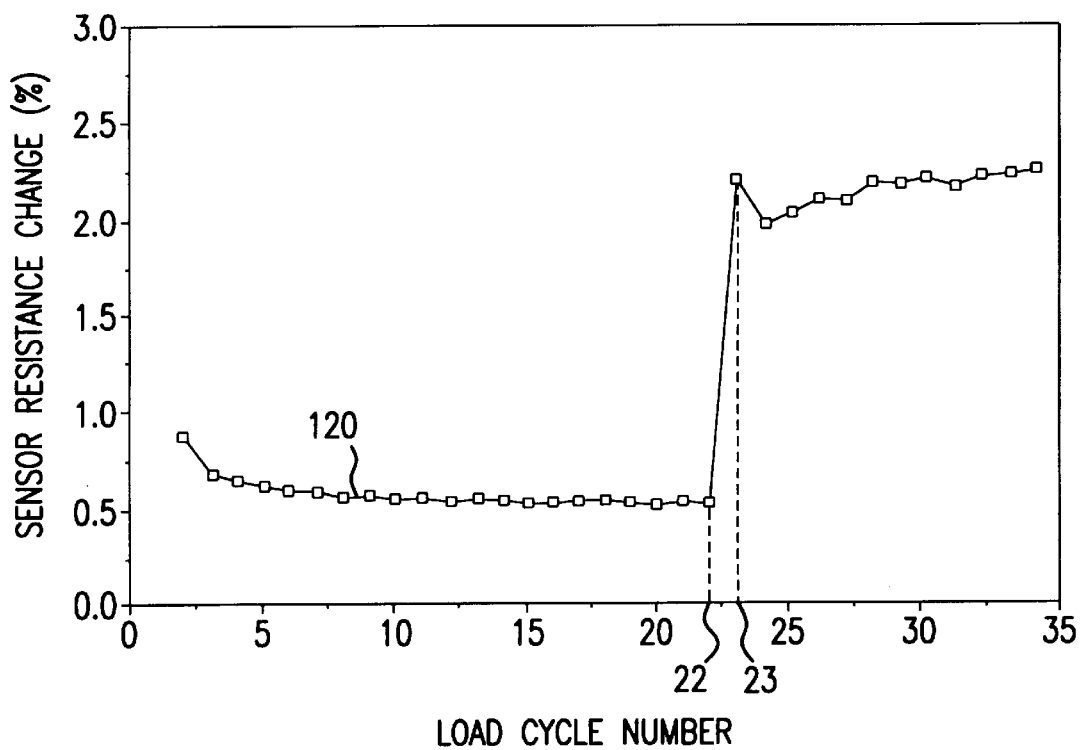
FIG. 14 is a graphical diagram illustrating chemical amplification of the sensor response in both oxygen-free and oxygen-containing environments.

Referring to FIG. 14, a graphical diagram is shown illustrating the percent sensor resistance change upon exposure to oxygen-free and oxygen-containing environments as a function of the number of loading cycles, with the sensor being regenerated after each loading cycle. In particular, the abscissa axis represents the loading cycle number, while the ordinate axis represents the percentage of change in resistance of the sensing element relative to the reference element. The first 22 loading cycles were performed in an oxygen-free environment, while the remaining loading cycles, beginning with the 23rd loading cycle, were performed in an oxygen-containing environment. As mentioned earlier, incomplete regeneration will result in a reduced sensing capacity for hydrogen sulfide. However, after a few cycles required to obtain steady state performance, the sensing element of the test device was consistently regenerated and operated in an oxygen-free environment as illustrated by the first 22 loading cycles of curve 120. Likewise, after a few cycles to obtain steady-state performance, the sensing element was consistently regenerated, as expected, in an oxygen-containing environment, as illustrated by subsequent loading cycles beginning with the 24th loading cycle of curve 120. During the 23rd cycle, the sensing element was regenerated in a nitrogen atmosphere, and then exposed to air prior to measurements of the hydrogen-sulfide-induced resistance change.

Also, the results of the test illustrate that there is over a fourfold increase in sensitivity in an oxygen-containing environment relative to an oxygen-free environment, as indicated by the jump in curve 120 between loading cycles 22 and 23. This demonstrates a chemical amplification of the response of test device in an oxygen-containing environment as opposed to an oxygen-free environment.

The basis of this chemical-amplification phenomenon is the different reaction mechanisms associated with the two types of gas streams. In an oxygen-free stream, hydrogen sulfide adsorbs on the gold surface of the sensing element and forms $H_2S$—Au bonds that are broken during the regeneration cycle, with the subsequent desorption of hydrogen sulfide. However, in an oxygen-containing stream, oxygen is reactive and thus can play a role both in the absorption and desorption processes. With respect to the adsorption process, oxygen clearly plays an important role, as illustrated in the large enhancement in sensor response during the 23rd cycle in FIG. 14 where the carrier-gas stream contained oxygen. With respect to the desorption process, during thermal regeneration the oxygen oxidizes hydrogen sulfide to form sulfur dioxide and water. However, this chemically assisted desorption apparently does not result in a substantially lower regeneration temperature, since the minimum voltage (11 volts) and time required for regeneration (5 seconds) were essentially the same for both oxygen-free and oxygen-containing streams. Since for conventional thermal regeneration a lower thermal regeneration temperature is expected for regeneration in an oxygen-containing environment, it appears that the electron bombardment associated with passing a current directly through the sensing element may provide an additional mechanism to effectively regenerate the sensing element under nearly the same conditions in either oxygen-free or oxygen-containing environments.

It is important to realize that the chemical amplification in an oxygen-containing environment is independent of the above regeneration mechanisms and should depend only upon the chemical nature of the sensing-element surface as well as hydrogen sulfide that is absorbed on the surface of the sensing element. Therefore, the over fourfold increase in sensor response observed for an oxygen-containing environment, as shown in FIG. 14, indicates that the sensing-element surface and/or the hydrogen sulfide must be chemically modified in the presence of oxygen to produce a substantially larger response than that in the absence of oxygen.

From the foregoing, it should be apparent that the disclosed amplification phenomenon and associated illustration in FIG. 14 has several advantages. First, the thin-metal-film sensing element can be regenerated in both oxidizing and reducing environments to extend its range of applications. Second, generating in a particular environment (e.g., oxidizing) can be advantageous in terms of substantially increasing the sensitivity of the sensing element. Third, the disclosed amplification of the sensor response in chemically different streams can be used as a diagnostic tool to characterize the nature of the stream (e.g., oxidizing or reducing).

Figure 15:
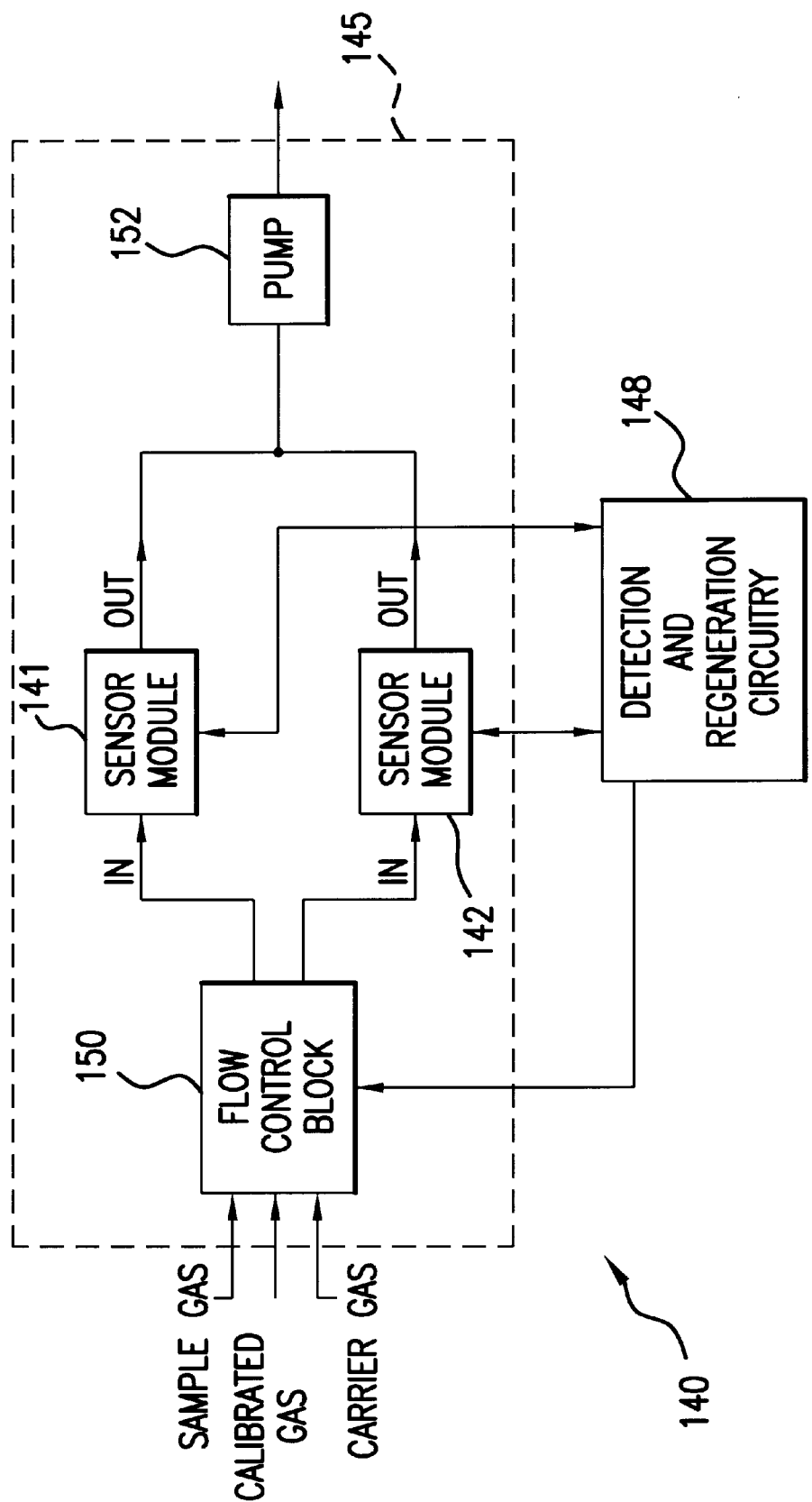
FIG. 15 is a detailed block diagram of an apparatus including a plurality of sensor modules for rapid and continuous detection of selected components in a fluid.

Apparatus for Intermittent and Continuous Detection of Selected Components in Gas Streams Referring to FIG. 15, a detailed block diagram of apparatus 140 is shown for rapid and continuous detection of selected chemical components in gas streams. The detection is rapid in the sense that measurements of a sampled gas are performed frequently in time, while the detection is continuous in the sense that the measurements are performed repeatedly over time. Apparatus 140 includes flow system 145 and detection and regeneration circuitry 148.

Flow system 145 includes a plurality of sensor modules 141 and 142, which are identical to sensor module 12 shown in FIGS. 1 and 7, for causing a change in the ratio of resistances of the sensing element relative to the reference element when selected components within a gas stream adsorb to the surface of the sensing element. Flow system 145 also includes flow control block 150 for receiving a plurality of gases and for controlling the concentration of selected components within a gas stream as well as the flow rate of the gas stream to sensor modules 141 and 142. Additionally, gas exiting modules 141 and 142 is pumped out of flow system 145 via pump 152.

Detection and regeneration circuitry 148 includes detection circuits similar to circuit 10 of FIG. 1 for each sensor module 141 and 142 for detecting the change in resistance of the sensing element relative to the reference element and converting such change into a measured concentration of the selected component in the gas stream. However, the detection circuits of circuitry 148 may differ slightly with that of circuit 10, wherein the MCU and operator interface components can be combined such that the same MCU and operator interface can be used for the detection circuits corresponding to both sensor modules 141 and 142.

Circuitry 148 also includes regeneration circuits for cleansing the sensing elements corresponding to each sensor module. The regeneration circuits may be either the constant-voltage regeneration circuit shown in FIG. 8 or the constant-current regeneration circuit shown in FIG. 10, or any combination thereof. Additionally, circuitry 148 is coupled to flow control block 150, wherein the MCU within circuitry 148 provides control signals to various solenoids of block 150, as will be discussed in detail below.

Figure 16:
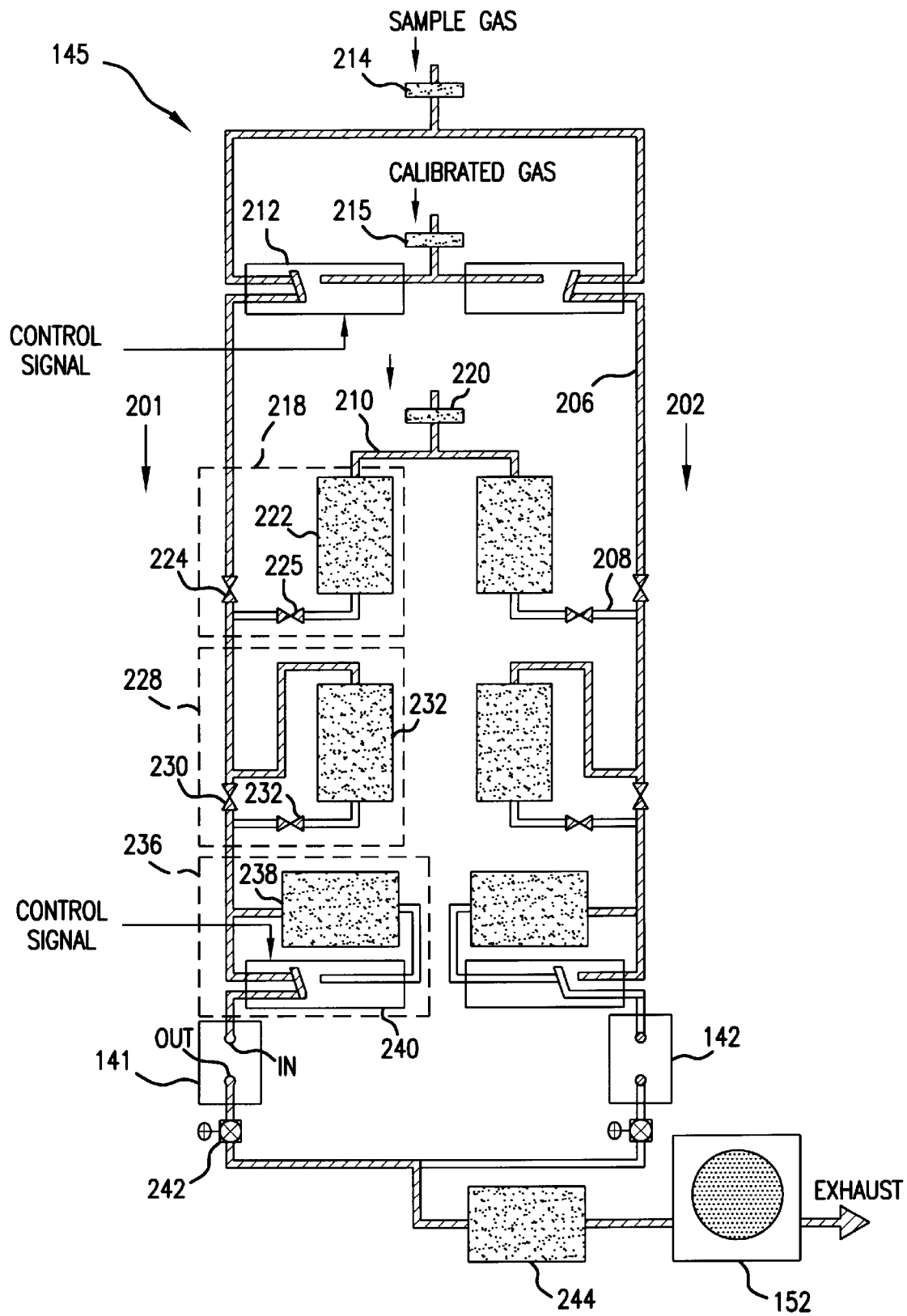
FIG. 16 is a detailed pictorial diagram illustrating the flow system of the apparatus of FIG. 16.

Referring to FIG. 16, a detailed pictorial diagram is shown illustrating flow system 145 of apparatus 140. FIG. 16 illustrates the flow system when two sensor modules (141 and 142) are used together with one carrier gas mixing stage and one dilution stage. The flow system includes two independent flow paths 201 and 202, whereby gas is drawn through the flow paths via pump 152. To more easily visualize the flow paths shown in FIG. 14, different gas streams types are printed in different typeface lines. For example, the dark bold typeface lines, such as line 206, indicates a gas stream that includes reactive components. The light typeface lines, such as line 208, indicates a scrubbed gas stream which is one that does not include any reactive components therein. Also, the medium typeface lines, such as line 210, indicates a carrier gas stream such as ambient air.

Since the components in flow path 201 are substantially identical to the components of flow path 202, only a discussion of the operation of flow path 201 is necessary. Gas selection solenoid 212 is responsive to a control signal from the MCU of circuitry 148 for selecting between sample gas and calibration gas. Both the sample and calibration gas streams respectively include particulate filters 214 and 215 for removing substantially large (>5 microns) particulates.

The gas stream then passes through a carrier-gas mixing segment 218 for mixing a carrier gas, such as ambient air, with the selected gas stream. In particular, the carrier gas passes through particulate filter 220 to remove particulates, and then through scrubbing filter 222 to remove any traces of reactant components that may exist in the carrier gas. The selected gas stream is then mixed with the scrubbed carrier gas via precision in-line orifices 224 and 225 that control the ratio of the carrier gas to be mixed with the selected gas stream.

The combined mixed gas stream then passes through dilution segment 228 for diluting the concentration of the reactive gas present in the gas stream. In particular, the mixed gas stream is split into two separate streams. One portion of the split gas stream is passed through scrubbing filter 232 for removing the reactive gas therein. Dilution is then accomplished by recombining both the scrubbed and the non-scrubbed portions of the split gas stream via precision in-line orifices 230 and 232. The dilution ratio may be varied by, for example, selecting the relative sizes of the orifices.

The recombined gas stream then passes into sampling segment 236 for providing a sample of the gas stream to sensor module 141. Sampling segment 236 includes scrubbing filter 238 and sampling solenoid 240. Solenoid 240 is responsive to a control signal from the MPU of circuitry 148 for selectively passing either scrubbed gas or gas that includes selected reactive components to sensor module 141. In particular, sampling solenoid 240 typically passes the output of scrubbing filter 238, which is gas that does not include selected components, to sensor module 141. However, during the sampling mode, solenoid 240 switches and passes the recombined gas stream that contains selected reactive components to sensor module 141, wherein the greater the time that solenoid 240 allows unscrubbed gas to pass through sensor module 141, the greater the sample size of gas containing reactive components. As described above, the selected reactive components that are present in the sampled gas stream will adsorb onto the surface of the sensing element, thereby increasing its resistance. However, the reactive components will not adsorb to the surface of the reference element, since its surface has been passivated. As a result, the change in resistance of the sensing element relative to the reference element is measured and converted to a concentration measurement of reactive components within the sampled gas via circuitry 148 in a similar manner as described above for circuit 10 of FIG. 1.

Upon exit from sensor module 141, the gas stream passes through precision needle valve 242 that controls the overall flow rate through flow path 201. Each of the independent gas streams is then recombined and passed through final scrubber filter 244 to remove residual contaminants, such as the removal of an acid gas-like hydrogen sulfide by passing it through a filter impregnated with a basic substance like sodium hydroxide, before passing through pump 152.

Although only two flow paths are shown in FIG. 16, it should be obvious that additional parallel flow paths similar to flow paths 201 and 202 leading to additional sensor modules can be readily incorporated into apparatus 140. Moreover, by providing multiple flow paths, each having corresponding sensor modules, continuous and uninterrupted sampling of a gas stream may be accomplished even when one or more sensor modules is undergoing regeneration or calibration, or even fails. Further, multiple flow paths allow for different flow-path parameters (i.e., dilution action and flow rate) to permit detection of both high and low concentrations in the same system. Also, a desired sampling frequency can be achieved by interleaving the sampling performed by different sensor modules.

Additionally, although only one sensing element and corresponding reference element are shown in the sensor module, it should be obvious that a sensor module may include a plurality of sensing and corresponding reference elements. Such redundancy would enable the module to remain active even though one of the elements within that module fails. Further, such redundancy would allow measured concentrations to be averaged, thereby increasing precision. Furthermore, in principle it is possible to measure one or more selected reactive components by using thin metal films that have different selectivities for the various reactive components in conjunction with the application of conventional pattern recognition algorithms. For example, gold, palladium, and gold-palladium alloy sensing elements exhibit different responses to hydrides such as hydrogen sulfide, arsine and phosphine.

Apparatus 140 achieves flexibility in measuring a wide dynamic range of concentrations of selected components as well as a wide range of sampling frequencies in several ways. First, by appropriately using additional dilution segments 228, dilution ratios up to 1000 for the selected component may be achieved. Second, the actual flow rate of gas through sensor module 141 can range from less than 1 cm$^3$/minute to several hundred cm$^3$/minute. Thus, the higher the flow rate, the more that the gas sample comes into contact with the sensing element for a given sampling time, thereby resulting in a greater exposure of the sensing element to the selected components. Third, the sampling time of the sampling solenoids can be varied from a minimum of about 0.1 seconds, which is constrained by the mechanical limitations of opening and closing the solenoid sampler valve, to a maximum limited only by the constraint of time between sequential samplings. In theory, by varying the dilution ratio, the flow rate and the sampling time as discussed above, over seven orders of magnitude in dynamic range can be achieved. Additionally, by minimizing the sampling time as well as the times set aside for stabilization prior to the reading of the signal before and after the solenoid is opened, a sampling frequency as high as 12 samples per minute can be achieved for a single sensor module. Even faster sampling frequencies can be obtained by overlapping the operation of two or more sensor modules.

Moreover, by operating the sensor at a current corresponding to a temperature intermediate between ambient temperature and the current required to reach the regeneration temperature, more rapid and continuous regeneration may be achieved. In particular, at intermediate temperatures, the sensor is partially regenerated, and a dynamic equilibrium is established wherein the reactive component is adsorbing to and desorbing from the surface of the sensor at equal rates. Increasing the concentration of reactive component will favor the adsorption process and cause an increase in sensor response, whereas decreasing the concentration of reactive component will favor the desorption process and cause a decrease in sensor response.

The sensor can be operated at a lower-intermediate temperature corresponding to a lower-intermediate current passing therethrough where the lower-intermediate temperature is one that is closer to ambient temperature than the regeneration temperature. During such a lower-intermediate temperature operation, the time required for regeneration is substantially reduced since the temperature need not be reduced to ambient temperature, while the sensitivity and dynamic range of the sensor is not substantially reduced.

Additionally the sensor can be operated at a higher-intermediate temperature corresponding to a higher-intermediate current passing therethrough where the higher-intermediate temperature is one that is closer to the regeneration temperature than ambient temperature. During such a higher-intermediate temperature operation, the sensor can be operated in a more continuous mode, and the sensor can be used to detect higher level concentrations of components. However, the sensitivity and dynamic range will be reduced relative to lower-temperature or ambient temperature operation. For example, for the gold-film sensors used to detect hydrogen sulfide, lower-temperature operation could be performed in the range 40–100° C., whereas higher-temperature operation could be achieved in the range 200–265° C.

An additional advantage of higher-intermediate temperature operation is discrimination against interfering components in the stream that may cause a sensor response at ambient temperature but are desorbed at higher temperatures. For example, mercury, nitrogen dioxide, and hydrogen sulfide all induce a response in a gold-film sensor at ambient temperature. However, since the desorption temperatures for these gases are approximately 200° C., 240° C. and above 265° C., respectively, only hydrogen sulfide would be detected at a higher-intermediate operating temperature above 240° C., but less than 265° C.

Apparatus 140 can be utilized to detect the presence of low levels of hydrogen sulfide in a sample of gas. For such detection, apparatus 140 is operated with a gas flow rate ranging between 3 cm$^3$/minute and 60 cm$^3$/minute, with a sampling time ranging from 0.15 seconds to 15 seconds. With no dilution or mixing modules used, detection in gas streams containing less than 1 part per billion (ppb) to over 300 ppb can be achieved. Additionally, with the incorporation of the dilution and mixing segments, gas streams with a concentration of several hundred parts per million (ppm) can be achieved.

Figure 17:
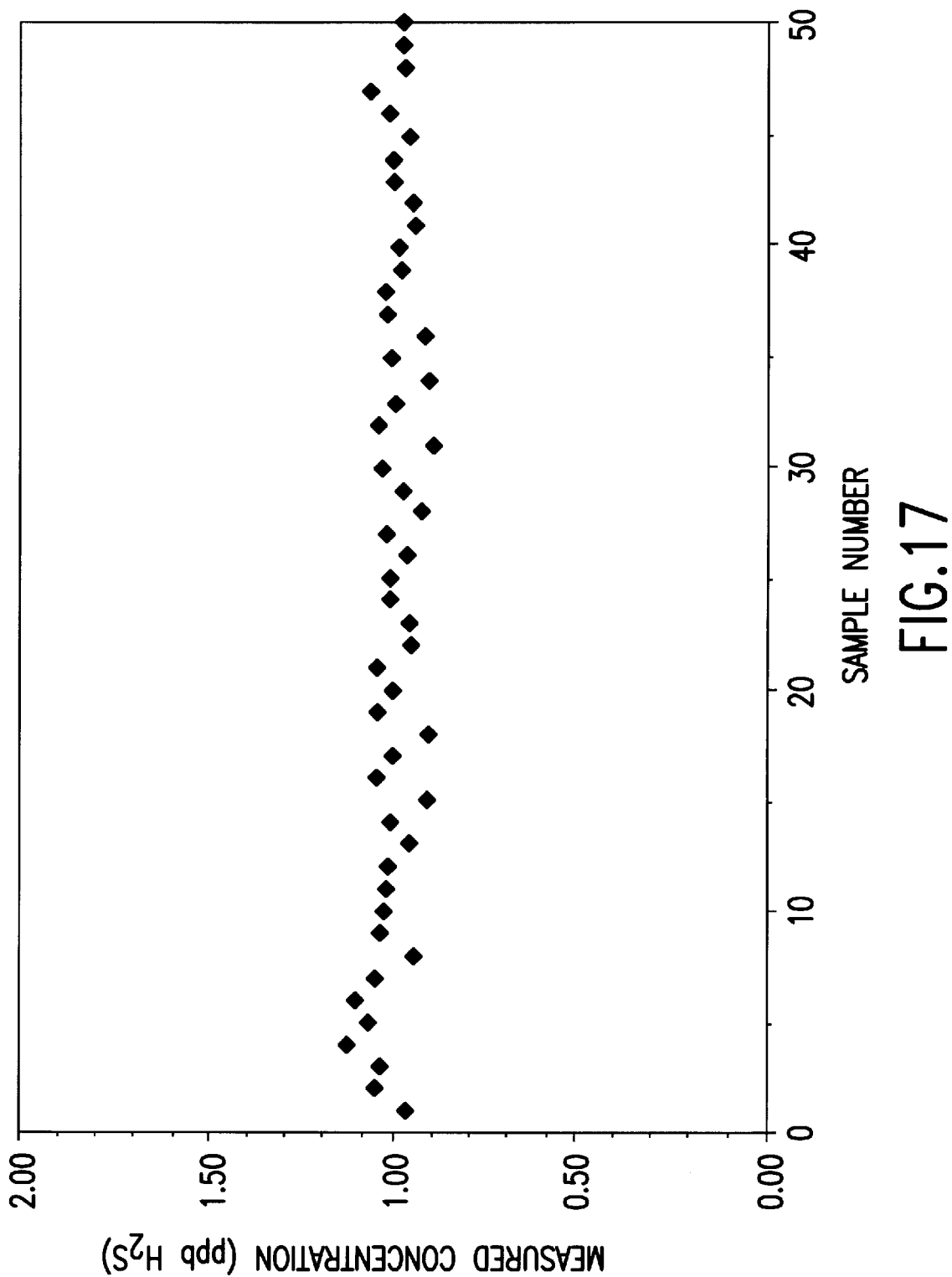
FIG. 17 is a graphical diagram illustrating test results of the apparatus of FIG. 16 for measuring the concentration of hydrogen sulfide in a calibrated gas stream containing 1 part per billion of hydrogen sulfide.

The performance of apparatus 140 has been demonstrated, the results of which are unprecedented for low-level measurements in the ppb range in terms of sensitivity, repeatability and accuracy. Referring to FIG. 17, a graphical diagram is shown illustrating the measured concentration of hydrogen sulfide for a calibrated gas stream containing an ultra-low level of only 1 ppb of hydrogen sulfide in air. The abscissa axis represents the sample number while the ordinate axis represents the measured concentration of hydrogen sulfide in ppb. There were 50 samples taken, and each sample included a 30-second exposure of a sensor module to the calibrated gas stream prior to regeneration. The precision of the measured concentration of an ultra low level of 1 ppb of hydrogen sulfide in a gas stream was outstanding. In particular, the arithmetic mean and standard deviation of the 50 samples were 1.00 and 0.05 ppb of hydrogen sulfide, respectively. Thus, in view of these results, apparatus 140 can be effectively used to detect components occurring in the very ultra-low level range of parts per trillion.

Figure 18:
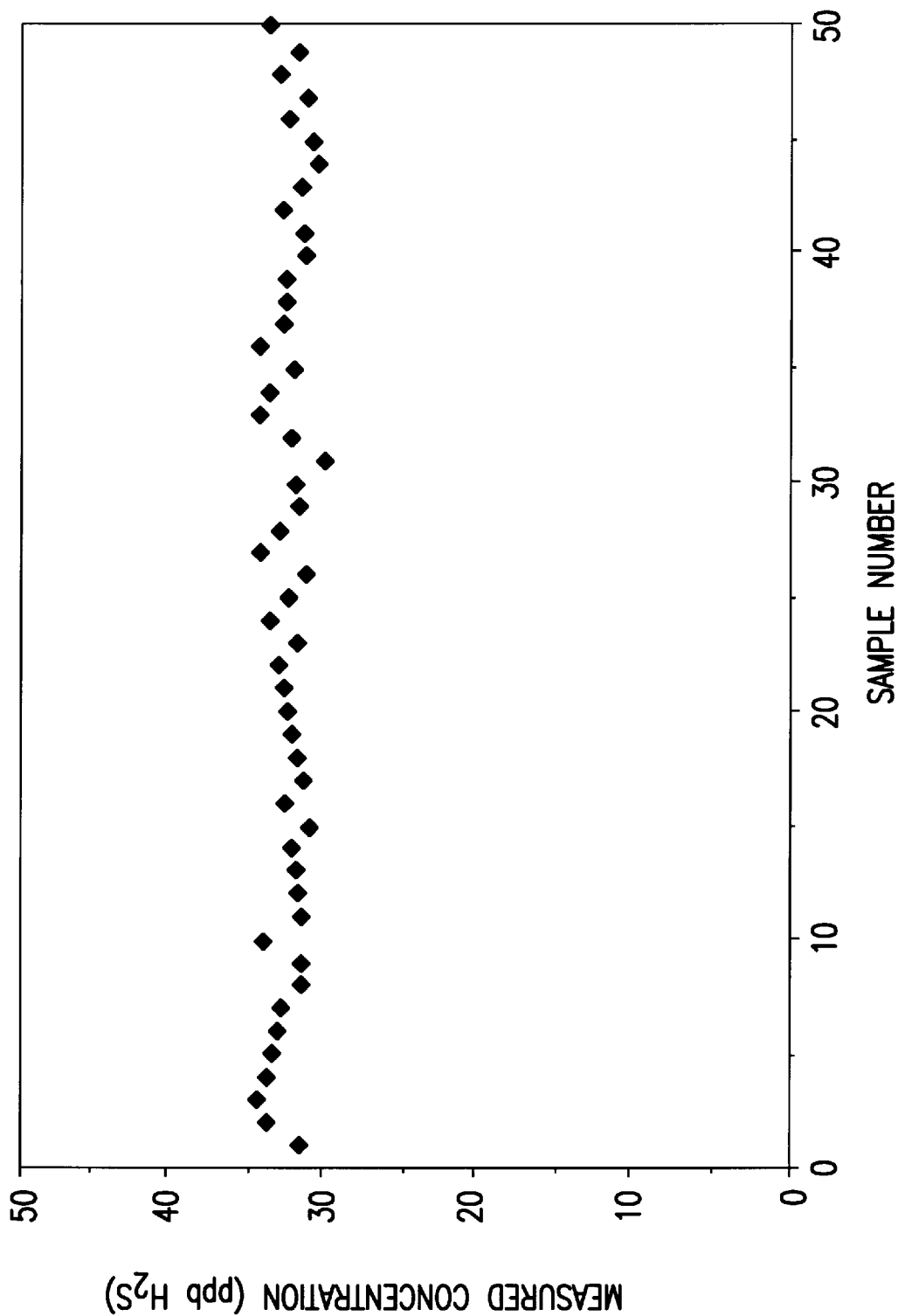
FIG. 18 is a graphical diagram illustrating test results of the apparatus of FIG. 16 for measuring the concentration of hydrogen sulfide in a calibrated gas stream containing 32.7 parts per billion of hydrogen sulfide.

Referring to FIG. 18, a graphical diagram is shown illustrating the measured concentration of hydrogen sulfide for a calibrated gas stream containing a low level of 32.7 ppb of hydrogen sulfide in air. The abscissa axis represents the sample number, while the ordinate axis represents the measured concentration of hydrogen sulfide in ppb. There were 50 samples taken, and each sample included a 2-second exposure of the sensor modules to the calibrated gas stream prior to regeneration. Here the arithmetic mean and standard deviation for the 50 samples were respectively 32.4 and 1.01 ppb.

Figure 19:
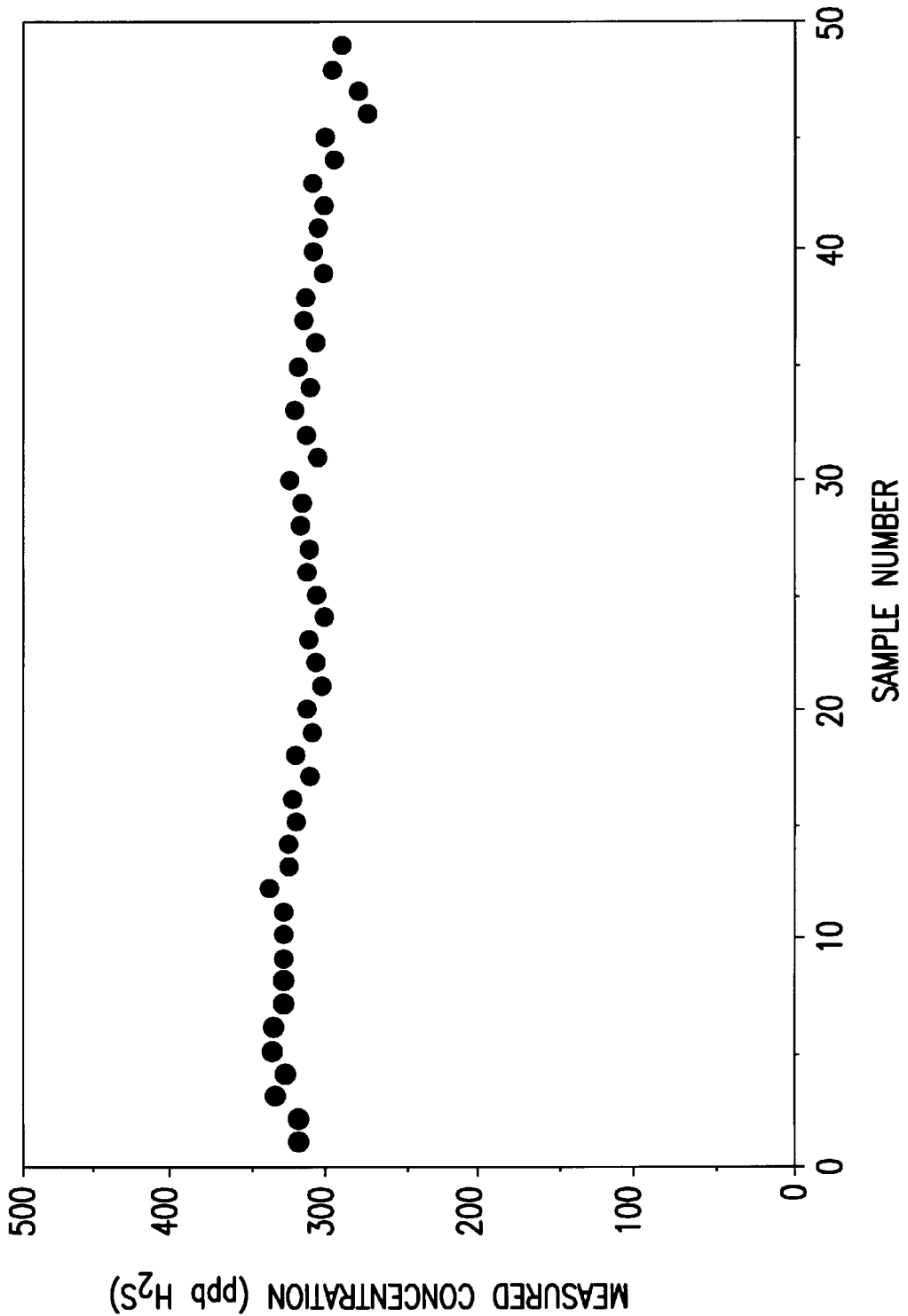
FIG. 19 is a graphical diagram illustrating test results of the apparatus of FIG. 16 for measuring the concentration of hydrogen sulfide in a calibrated gas stream containing 323 parts per billion of hydrogen sulfide.

Referring to FIG. 19, a graphical diagram is shown illustrating the measured concentration of hydrogen sulfide for a calibrated gas stream containing a higher level of 323 ppb of hydrogen sulfide in air. The abscissa axis represents the sample number while the ordinate axis represents the measured concentration of hydrogen sulfide in ppb. There were 50 samples taken, and each sample included a 0.5-second exposure of the sensor modules to the calibrated gas stream prior to regeneration. The arithmetic mean and standard deviation of the 50 samples were respectively 326 and 8.0 ppb.

Figure 20:
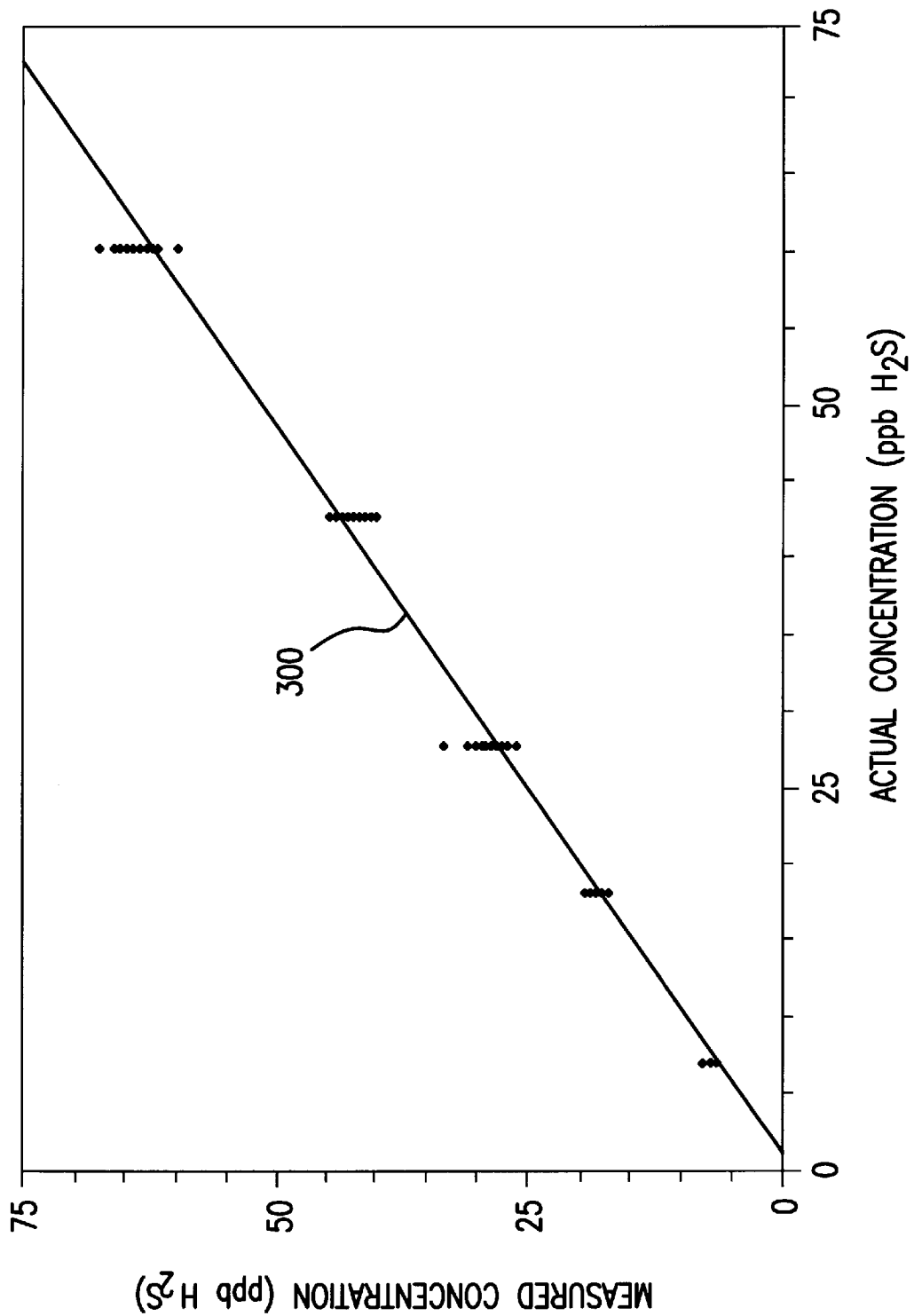
FIG. 20 is a graphical diagram illustrating measured concentration levels of hydrogen sulfide by the apparatus of FIG. 16 versus a wide range of actual concentration levels of hydrogen sulfide.

Finally, referring to FIG. 20, a graphical diagram is shown illustrating a comparison between the measured and actual concentrations of hydrogen sulfide. The abscissa axis represents the actual concentration of hydrogen sulfide in ppb, while the ordinate axis represents the measured concentration of hydrogen sulfide in ppm as determined by apparatus 140 via hydrogen sulfide permeation tubes traceable to standards available from the National Institute of Standards and Technology. The results of FIG. 20 as well as FIGS. 17–19 clearly indicate the precision of apparatus 140 in measuring a wide range of concentrations of hydrogen sulfide in a sample of gas. In particular, these results clearly demonstrate that the sensor modules can be used with high accuracy and reproducability to measure hydrogen sulfide concentrations in the very low ppb range. Additionally, the sensor modules can be used to measure hydrogen sulfide concentrations in the several hundred ppm range. This is important for industrial hygiene and health applications, since hydrogen sulfide in the ppm range is the largest cause of occupational sudden death.

The need to control the levels of sulfur in hydrocarbon streams on a more real-time basis is becoming critical in the refinery and petrochemical industries, since sulfur is the primary impurity and environmental pollutant in coal, oil, liquid fuels and natural gas. Furthermore, since many catalysts used in refining are poisoned by sulfur at levels as low as 500 ppb, measurement and control of the sulfur levels in such streams at concentrations in the ppb range is important for catalyst protection.

Apparatus 140 of the present invention has the ability to analyze the total sulfur content in gaseous and liquid streams when combined with a sample conditioning system for converting liquid streams into gaseous streams as well as the sulfur-containing molecules to hydrogen sulfide. This can be accomplished by conventional pyrolysis by complete oxidation of the stream in oxygen gas or air followed by reduction of the stream in hydrogen gas. Catalysts may also be employed to reduce the rather extreme conditions required for complete pyrolysis of the stream.

Figure 21:
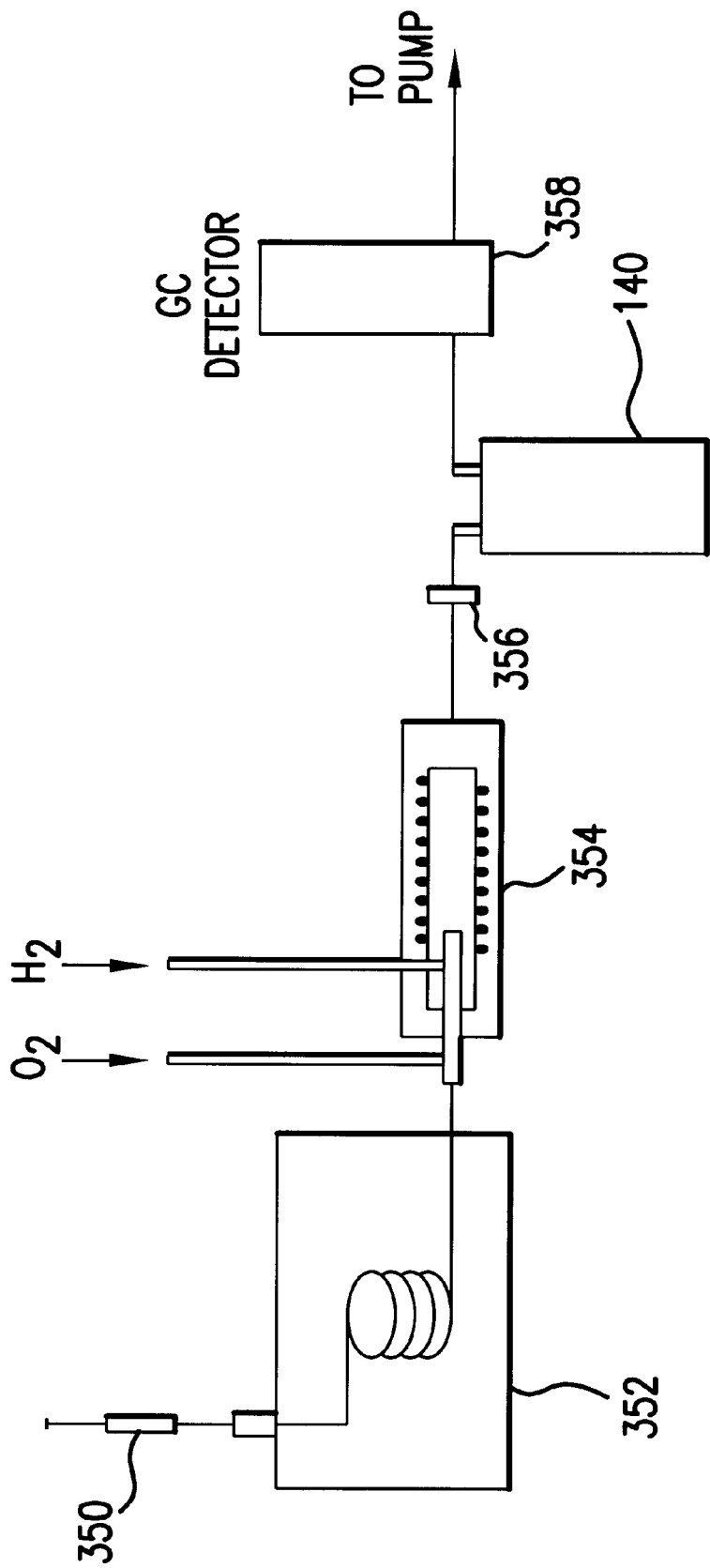
FIG. 21 is diagram of a system including the apparatus of FIG. 15 for detecting the total sulfur content in liquid streams.

The test system for the analysis of the total sulfur content in liquid streams is shown in FIG. 21. The test system included the injection of a liquid hydrocarbon sample via syringe 350 into a partial vacuum (about 140 torr) to minimize the condensation of water in the system. Water removal can also be accomplished by passing the gas to be analyzed through a condenser, which permits operation under ambient pressure conditions.

Next, the stream is passed through gas chromatograph (GC) 352, which separates the different chemical components in the stream, to allow a comparison of apparatus 140 to the performance of GC detector 358.

The stream is then passed through pyrolyzer 354 for converting all sulfur-containing molecules in the stream to hydrogen sulfide by first completely oxidizing with oxygen, and then completely reducing with hydrogen, the stream. This configuration allows a direct on-line comparison of the performance of apparatus 140 to a current analytical state-of-the-art means of detecting sulfur by using a commercial gas chromatography chemiluminescence detector. The stream is then passed through pre-filter 356 for removing before being introduced to apparatus 140.

Standard samples of thiophene in iso-octane were used containing 579, 57.9, 5.8 and 1.15 ppm by weight of sulfur and were injected using a 1 microliter standard gas chromatography syringe. Since the elution time for the hydrogen sulfide was approximately 345 seconds and was less than 20 seconds in width, the sampling time was set to give a sample cycle time of 64 seconds, so that the entire hydrogen sulfide peak would be contained within the sixth sample cycle (320 to 384 seconds of elapsed time). Blank injections of iso-octane were used to establish the baseline, and the mean baseline was subtracted from the sensor response.

Figure 22:
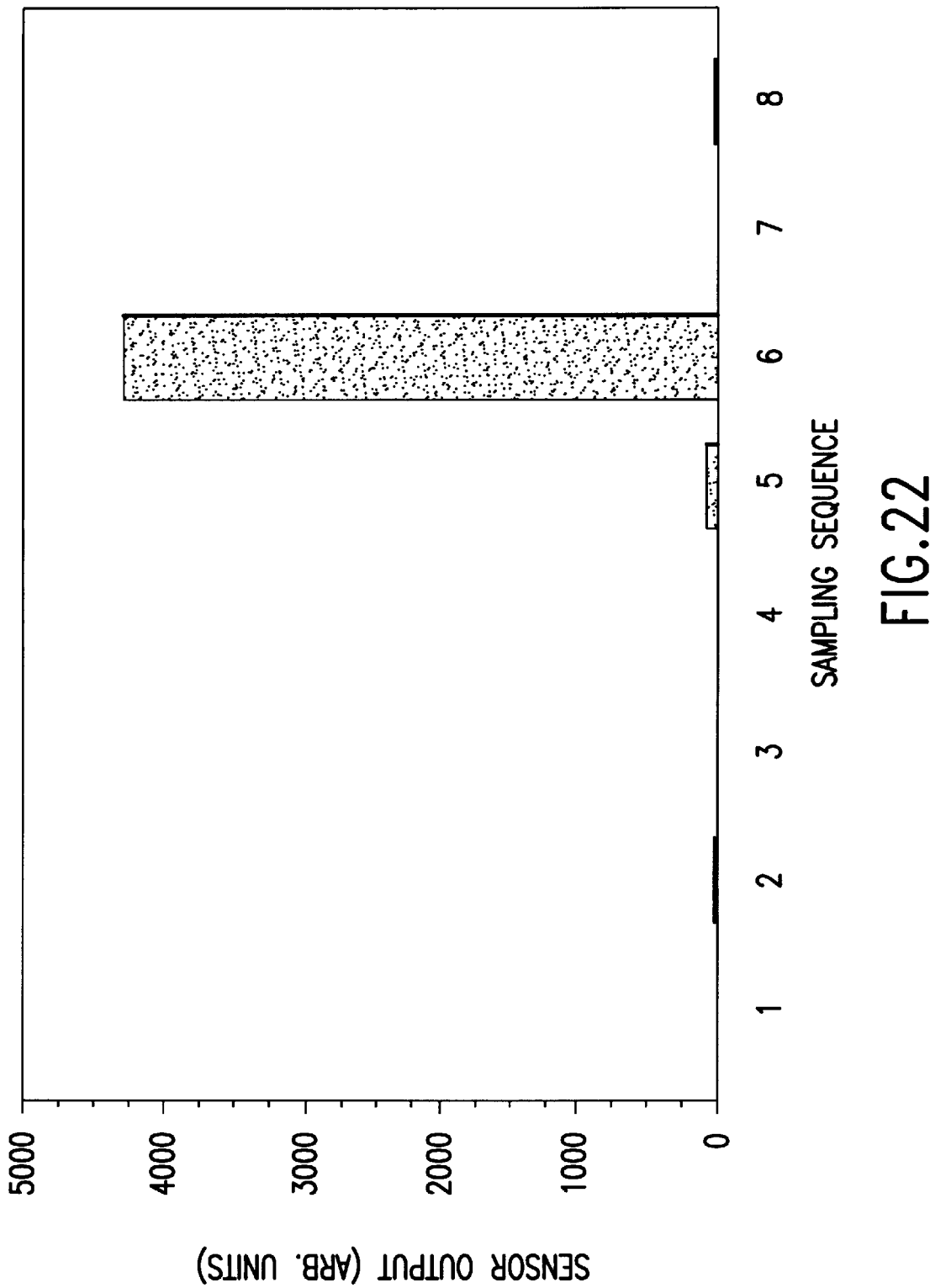

Referring to FIGS. 22 and 23, bar-chart diagrams are shown illustrating the sensor module responses to 579 and 1.15 ppm by weight of sulfur in iso-octane, respectively. The abscissa axis for FIGS. 22 and 23 represents the sampling sequence while the ordinate axis represents the sensor module output in arbitrary units. From FIG. 23, it is evident that levels as low as 1 ppm of total sulfur in hydrocarbon liquids can be measured under the conditions of this experiment, wherein the sensitivity is within a factor of three to that of the chemiluminescence chromatography detector. Also, by increasing the amount of liquid sample injected, or preferably by incorporating continuous sample injection, it should be feasible to detect sulfur in liquid hydrocarbons as low as in the ppb range. Additionally, from FIG. 22, it is evident that sulfur levels in the several hundred ppm range can be also be measured.

By now it should be apparent from the foregoing discussion that a novel method and apparatus for restoring the sensing capacity of a sensing element composed of a thin film of metal has been provided. The present invention performs regeneration by passing an electrical current through the sensing element for a predetermined time interval to remove accumulated components that have adsorbed onto the surface of the sensing element due to the sensing element's affinity for the components. The passing of current through the sensing element can be accomplished either by applying a constant voltage across the sensing element or by forcing a constant current through the sensing element. This current through the sensing element can remove the components from the sensing element by a combination of resistive heating of the element and electron bombardment of the components on the surface of the element. This current regeneration can be performed in both oxygen-containing and oxygen-free environments. However, the sensitivity of the sensing element is substantially enhanced in an oxygen-containing environment for chemically reducing reactive components such as hydrogen sulfide, as opposed to an oxygen-free environment such as nitrogen.

Moreover, to prevent possible rupture of the sensing element due to electromigration, the current may be alternated in a first direction and then in a second and opposite direction through the sensing element in sequential runs of equal predetermined time intervals. Because heating is accomplished by passing a current directly through the sensing element, rather than special heater elements interposed between the thin films of the sensing element and the reference element, both of these films can be placed in close proximity on the same side of a substrate. This allows the two elements to be wire bonded in a considerably more compact configuration. With the interleaved heater configuration of the prior art, on the other hand, wire bonding capability is unavailable.

It should also be apparent that the present invention provides a method for creating a reference element. The reference element is passivated by a layer of molecular thickness by saturating the surface of the reference element with reactive components that adsorb to its surface when contacted. This makes the reference element inert to further exposure to the reactive components. Additionally, because a relatively thick layer of material such as chromia is not formed on the surface of the reference element, the reference element has a temperature coefficient substantially identical to that of a corresponding sensing element. Also, such a reference element is dynamic because it can be easily converted back into an active sensing element by regenerating the reference element and desorbing the reactive components from the reference element. The regeneration may be accomplished by, for example, current-driven regeneration.

It should also be apparent that the present invention provides an apparatus for intermittent or continuous detection of selected components. The apparatus includes a plurality sensor modules each including sensing and reference elements, such that, when selected chemical components in a gas stream have adsorbed to the surface of the sensing element, a change in the ratio of resistances of the sensing element relative to the reference element results.

The apparatus also includes electronic circuitry for detecting the change in ratio of resistances of the sensing element relative to the reference element and for converting such change into a measured concentration of the selected component within the gas stream. The electronic circuitry further includes regeneration circuits for providing both constant-voltage and constant-current regeneration.

Also, the apparatus includes a flow system for controlling the concentration of the selected component in a gas stream, the flow rate of the gas stream, and the time that a gas stream containing the selected component flows to the sensor modules.

Although certain preferred embodiments and methods have been disclosed herein, it will be apparent from the foregoing disclosure to those skilled in the art that variations and modifications of such embodiments and methods may be made without departing from the true spirit and scope of the invention. Accordingly, it is intended that the invention shall be limited only to the extent required by the appended claims and the rules and principles of applicable law.

What is claimed is:

1. A method for restoring the sensing capacity of an electrically conductive thin metal film sensing element having a first and second node employed for detection of a predetermined component in a fluid mixture the sensing element having a sensing current passing therethrough, wherein the predetermined component is accumulated on the surface of the sensing element, comprising the steps of:

passing a regeneration electrical current which is greater than the sensing current through the sensing element between the first and second node for a predetermined time interval, wherein a potential is created between the first and second node; and heating the sensing element via the regeneration electric current to a temperature sufficient to cleanse the component from the sensing element, wherein the sensing element performs the heating function.

2. The method according to claim 1 wherein the predetermined component is hydrogen sulfide.

3. The method according to claim 1 wherein the sensing element comprises a noble metal.

4. The method according to claim 1 wherein passing an electrical current through the sensing element includes applying a constant voltage across the sensing element.

5. The method according to claim 4 wherein the sensing element is composed of gold and wherein the constant voltage is approximately 11 volts.

6. The method according to claim 1 wherein passing an electrical current through the sensing element includes applying a constant direct current through the sensing element.

7. The method according to claim 6 wherein the sensing element is composed of gold and wherein the constant current is approximately 65 milliamps.

8. The method according to claim 1 wherein passing an electrical current through the sensing element includes alternately passing said current in a first direction of flow for a predetermined time interval and passing said current in a second and opposite direction of flow for an equal predetermined time interval thereby inhibiting electromigration and rupture of the thin metal film of which the sensing element is composed.

9. The method according to claim 8 wherein the sensing element is composed of gold, wherein an alternating voltage of approximately 11 volts is applied across the sensing element, and wherein the predetermined time interval is approximately 5 seconds.

10. The method according to claim 8 wherein the sensing element is composed of gold, wherein an alternating current of approximately 65 milliamps is applied through the sensing element.

11. The method according to claim 1 wherein the sensing element is heated to an intermediate temperature between ambient temperature and temperature sufficient to cleanse the components from the sensing element.

12. The method according to claim 11 wherein the intermediate temperature is closer to the ambient temperature than to the temperature sufficient to cleanse the component from the sensing clement to not substantially reduce the sensitivity of detection of the predetermined component by the sensing element.

13. The method according to claim 11 wherein the intermediate temperature is closer to the temperature sufficient to cleanse the component from the sensing clement than to the ambient temperature thereby permitting detection of the predetermined component at higher concentration levels and improved discrimination against interfering components.

* * * * *

UNITED STATES PATENT AND TRADEMARK OFFICE
CERTIFICATE OF CORRECTION

PATENT NO. : 5,985,673

DATED : November 16, 1999

INVENTOR(S) : Bao et al.

It is certified that error appears in the above-identified patent and that said Letters Patent is hereby corrected as shown below:

On the Title Page:

[56] References Cited, OTHER PUBLICATIONS: Under Kayser et al., "Vapvr" should read -- Vapor -- ;

In the Specification:

Column 5, line 16: "cross sectional" should read -- cross-sectional -- ;
Column 5, line 19: "cross sectional" should read -- cross-sectional -- ;
Column 5, line 22: "cross sectional" should read -- cross-sectional -- ;
Column 8, line 4: "absorbed" should read -- adsorbed -- ;
Column 8, line 14: "if" should read -- of -- ;
Column 8, line 23: "absorbed" should read -- adsorbed -- ;
Column 8, line 25: "absorb" should read -- adsorb -- ;
Column 8, line 39: "three dimensional" should read -- three-dimensional -- ;
Column 9, line 10: "cross" should read -- cross- -- ;
Column 9, line 11: "cross" should read -- cross- -- ;
Column 10, line 30: "cross sectional" should read -- cross-sectional -- ;
Column 11, line 30: "is" should read -- are -- , and "cross" should read -- cross- -- ;
Column 17, line 27: "absorbed" should read -- adsorbed -- ;
Column 19, line 65: "absorbed" should read -- adsorbed -- ;
Column 20, line 33: "cycle,the" should read -- cycle, the -- ;
Column 20, line 52: "absorption" should read -- adsorption -- ; and
Column 21, line 20: "absorbed" should read -- adsorbed -- .

Signed and Sealed this

Twenty-seventh Day of March, 2001

Attest:

NICHOLAS P. GODICI

*Attesting Officer*     *Acting Director of the United States Patent and Trademark Office*